(12) United States Patent
Granot et al.

(10) Patent No.: US 8,527,242 B2
(45) Date of Patent: Sep. 3, 2013

(54) METHODS AND DEVICES FOR ANALYZING MATERIAL PROPERTIES AND DETECTING OBJECTS IN SCATTERING MEDIA

(75) Inventors: Er'el Granot, Herzliya (IL); Shmuel Sternklar, Rehovot (IL); Yosef Ben-Aderet, Ashkelon (IL)

(73) Assignee: Ariel—The University Company for Research and Development, Ltd., Ariel (IL)

( * ) Notice: Subject to any disclaimer, the term of this patent is extended or adjusted under 35 U.S.C. 154(b) by 193 days.

(21) Appl. No.: 12/865,759

(22) PCT Filed: Feb. 8, 2009

(86) PCT No.: PCT/IL2009/000143
§ 371 (c)(1),
(2), (4) Date: Aug. 2, 2010

(87) PCT Pub. No.: WO2009/098694
PCT Pub. Date: Aug. 13, 2009

(65) Prior Publication Data
US 2011/0022328 A1    Jan. 27, 2011

(30) Foreign Application Priority Data
Feb. 7, 2008  (IL) .......................................... 189352

(51) Int. Cl.
*G06F 19/00* (2011.01)
(52) U.S. Cl.
USPC ........................................................ 702/189
(58) Field of Classification Search
USPC ....................................................... 702/189
See application file for complete search history.

(56) References Cited

U.S. PATENT DOCUMENTS

2005/0012934 A1*  1/2005  Szafraniec ................... 356/484

OTHER PUBLICATIONS

Er'el Granot, Reconstructing the impulse response of a diffusive medium with the Kramers—Kronig relations, Apr. 12, 2007, Optical Society of America, p. 1620-1626.*
Granot et al., Reconstructing the impulse response of a diffusive medium with the Kramers-Kronig relations, Journal of the Optical Society of America, Jul. 2007, pp. 1622-1625, vol. 24, No. 7, U.S.A.
Granot et al., Quasi-ballistic imaging through a dynamic scattering medium with optical-field averaging using Spectral-Ballistic-Imaging, Optics Express, Sep. 18, 2006, 8598-8603, vol. 14, No. 19, U.S.A., pp. 4-6.
Lucarini et al., Multiply subtractive generalized Kramers-Kronig relations: Application on third-harmonic generation susceptibility on polysilane, Journal of Chemical Physics, Dec. 1, 2003, 11095-11098, vol. 119, No. 21, pp. 4-6.
International Search Report dated May 22, 2009 in corresponding International Application No. PCT/IL2009/000143.
Written Opinion dated May 22, 2009 in corresponding International Application No. PCT/IL2009/000143.

* cited by examiner

*Primary Examiner* — Tung S Lau
(74) *Attorney, Agent, or Firm* — Browdy and Neimark, PLLC

(57) ABSTRACT

Disclosed is a method for determining an phase spectrum $\theta(\omega)$ of the complex spectral transfer function $H(\omega)$ of a medium. In some embodiments, the method is applied for detecting or imaging an object screened by scattering medium or for determining a refractive index spectrum of a material.

11 Claims, 9 Drawing Sheets

METHODS AND DEVICES FOR ANALYZING MATERIAL PROPERTIES AND DETECTING OBJECTS IN SCATTERING MEDIA

RELATED APPLICATIONS

The present application gains priority from Israel Patent Application Nr. 189,352 filed February 2008, which is included by reference as if fully set forth herein, and is taken together with the 10 contents herein to fully describe aspects of the invention.

Some embodiments of the present invention are related to the teachings of WO 2004/008116 (Ref. 16) and "Differential multiply subtractive Kramers-Kronig relations," by the Inventors in J. Opt. Soc. Am. B 25, 609-613 (2008) published 27 Mar. 2008 (Ref. 23) both which are included by reference as if fully set-forth herein.

FIELD OF THE INVENTION

Some embodiments of the invention relate to the field of electromagnetic spectroscopy and imaging. Specifically, some embodiments relate to acquiring the amplitude and phase spectrum of a medium or an object, e.g. the frequency-dependent spectrum, in order to characterize spectral properties of the medium or object and/or to image objects screened by a scattering medium.

BACKGROUND OF THE INVENTION

Publications and other reference materials referred to herein, including reference cited therein, are incorporated herein by reference in their entirety and are numerically referenced in the following text and respectively grouped in the appended Bibliography which immediately precedes the claims.

Many applications would benefit from a fast and robust technique for acquiring the amplitude and phase spectrum of a medium. In addition, in many industrial applications, it is imperative to know the refractive-index dependence of an element or device on electromagnetic frequency, i.e. the dispersion. There is a growing demand to accurately analyze the linear and nonlinear spectra of bulk and composite materials (e.g. absorption, refractive index, Rayleigh, fluorescence, Raman, etc.), both in the areas of engineering as well as in the life sciences.

The Kramers-Kronig (KK) relations were derived in 1926/7 [Refs. 1, 2] to calculate the refractive index of a medium by its absorption measurements i.e., by a transmission or reflection spectrum measurement. Although the KK relations are merely a mathematical derivation, they have led to profound scientific capabilities, since they bridge two physical parameters that require different experimental methodologies when measured separately. Since it is usually much simpler to measure the absorption coefficient than the refractive index, mathematical relations like the KK ones, which relate the refractive index to the absorption coefficients are very appealing [Ref. 3].

In fact, the KK relations are only a special case of a very broad family of Hilbert transforms. The Hilbert transform connects the real and imaginary parts of the Fourier transform of any causal square-integrable $L^2$ function $\alpha(t)$. If $\alpha(t)$ is real then the Hilbert transform can be rewritten (see, for example, Ref. 3)

$$\mathrm{Re}\{a(\omega)\} = \frac{2}{\pi} P \int_0^\infty \frac{\omega' \mathrm{Im}\{a(\omega')\}}{\omega'^2 - \omega^2} d\omega' \quad (1a)$$

$$\mathrm{Im}\{a(\omega)\} = -\frac{2\omega}{\pi} P \int_0^\infty \frac{\mathrm{Re}\{a(\omega')\}}{\omega'^2 - \omega^2} d\omega' \quad (1b)$$

where P stands for Cauchy's principal value.

Therefore, the KK relations can be used to reconstruct the spectral transfer function $H(\omega)=|H(\omega)|e^{i\theta(\omega)}$ of a medium by measuring only the amplitude of the spectrum $|H(\omega)|$, i.e., instead of applying the KK relations to the complex refractive index, one can implement it on the logarithm of the complex transfer function:

$$\ln[H(\omega)] = \ln|H(\omega)| + i\theta(\omega) \quad (2)$$

The KK relations can then be rewritten [3]

$$|H(\omega')| = \frac{2}{\pi} P \int_0^\infty \frac{\omega' \theta(\omega')}{\omega'^2 - \omega^2} d\omega' \quad (3)$$

$$\theta(\omega) = -\frac{2\omega}{\pi} P \int_0^\infty \frac{\ln|H(\omega')|}{\omega'^2 - \omega^2} d\omega' \quad (4)$$

Recently, it has been suggested by the inventors [Ref. 4] to use the KK relation to reconstruct the impulse response of a diffusive medium, i.e. a medium which scatters the radiation such as biological tissue, clouds, smoke, cloth, etc. Such reconstructions are important in diffusive medium imaging, since they can allow, for example, distinguishing between the ballistic i.e. unscattered or 'first' light, the quasi-ballistic, and the diffusive light. Applications for the detection and imaging of a material's composition within a diffuse media include detection of tumors or build-up of plaque within tissue, or objects hidden by cloud cover, smoke or cloth. Clearly, the diffusive light is responsible for the blurring of the image [Refs. 5-9]. The main advantage of the approach proposed in [Ref. 4] is that the amplitude of the transfer function is easily measured, while phase measurements can be more complicated and time consuming. Therefore, the amplitude $|H(\omega)|$ is measured in a finite spectral range $\omega_L \leq \omega \leq \omega_H$ (actually, its square is measured, i.e., the intensity $I(\omega)=|H(\omega)|^2$) and the phase is reconstructed accordingly [Ref. 10]

$$\theta_{KK}(\omega) = -\frac{2\omega}{\pi} P \int_{\omega_L}^{\omega_H} \frac{\ln|H(\omega')|}{\omega'^2 - \omega^2} d\omega', \quad (5)$$

$$\text{or } \theta_{KK}(\omega) = -\frac{\omega}{\pi} P \int_{\omega_L}^{\omega_H} \frac{\ln|I(\omega')|}{\omega'^2 - \omega^2} d\omega',$$

so that the final reconstructed transfer function is then $$H_{KK}(\omega) = |H(\omega)| \exp[i\theta_{KK}(\omega)] \text{ or } H_{KK}(\omega) = \sqrt{I(\omega)} \exp[i\theta_{KK}(\omega)] \quad (6)$$

The main problem with the method proposed in [Ref. 4] is the fact that the measured spectrum is always finite, and therefore the phase reconstruction may not be accurate. In fact, the integrand in Eq. (5) decays for large $\omega'$ and in some cases (when the spectral range is wide enough) this approximation is sufficient for the reconstruction (see, for example, Ref. 10). It should be noted that the KK relations for transfer function reconstruction converge faster than in the case of index refraction reconstruction. In the former case Eq. (4) is used, which converges as $\omega'^{-2}$. On the other hand, in the latter case an equation of the form (3) is used, which converges as $\omega'^{-1}$. However, for many applications the convergence is not fast enough, leading to large error.

To improve the convergence it was suggested to derive the phase with knowledge of specific measurements ("anchoring" points) at certain "anchoring" frequencies. By doing so the power of $\omega'$ at the denominator of Eq. (5) increases, and the convergence is improved. This technique was developed by Bachrach and Brown [Ref. 11] and Ahrenkiel [Ref. 12] and later by Palmer, Williams, and Budde [Ref. 13] and is usually called the multiply subtractive KK relation (MSKK). Specifically, if the phase is known at Q different frequencies, i.e., $\theta(\omega_1), \theta(\omega_2), \ldots \theta(\omega_Q)$ then the phase can be evaluated by the relation $$\frac{\theta(\omega)}{\omega} = \frac{\theta(\omega_1)}{\omega_1} \frac{(\omega^2 - \omega_2^2)(\omega^2 - \omega_3^2) \ldots (\omega^2 - \omega_Q^2)}{(\omega_1^2 - \omega_2^2)(\omega_1^2 - \omega_3^2) \ldots (\omega_1^2 - \omega_Q^2)} + \qquad (7)$$

$$\ldots \frac{\theta(\omega_j)}{\omega_j} \frac{(\omega^2 - \omega_1^2) \ldots (\omega^2 - \omega_{j-1}^2)(\omega^2 - \omega_{j+1}^2) \ldots (\omega^2 - \omega_Q^2)}{(\omega_j^2 - \omega_1^2) \ldots (\omega_j^2 - \omega_{j-1}^2)(\omega_j^2 - \omega_{j+1}^2) \ldots (\omega_j^2 - \omega_Q^2)} + $$

$$\ldots \frac{\theta(\omega_Q)}{\omega_Q} \frac{(\omega^2 - \omega_1^2)(\omega^2 - \omega_2^2) \ldots (\omega^2 - \omega_{Q-1}^2)}{(\omega_Q^2 - \omega_1^2)(\omega_Q^2 - \omega_2^2) \ldots (\omega_Q^2 - \omega_{Q-1}^2)} - $$

$$\frac{2}{\pi}(\omega^2 - \omega_1^2)(\omega^2 - \omega_2^2) \ldots (\omega^2 - \omega_Q^2) P$$

$$\int_0^\infty \frac{\ln|H(\omega')|}{(\omega'^2 - \omega^2)(\omega'^2 - \omega_1^2) \ldots (\omega'^2 - \omega_Q^2)} d\omega'$$

The first terms resemble the Legendre polynomial interpolation, and only the last term (with the integral) takes account of the function's causality. In this case the integral converges as $\omega'^{-2Q}$ so that it will converge for a narrower spectrum. In the particular case of singly subtractive KK (SSKK) relations [Refs 3, 11], i.e., when only a single 'anchoring' point is known, this expression reduces to $$\frac{\theta(\omega)}{\omega} = \frac{\theta(\omega_1)}{\omega_1} - \frac{2}{\pi}(\omega^2 - \omega_1^2) P \int_0^\infty \frac{\ln|H(\omega')|}{(\omega'^2 - \omega^2)(\omega'^2 - \omega_1^2)} d\omega' \qquad (8)$$

As was demonstrated in the literature [Ref. 3] this technique improves the reconstruction for less than infinite spectral boundaries, i.e. in the finite range $\omega_L \leq \omega \leq \omega_H$. However, the main disadvantage of this technique is that in most cases there is absolutely no a-priori information on the phases, and since phase measurements are difficult to carry out it may be difficult to implement this promising technique.

The inventors have developed in the past a technique known as Spectral Ballistic Imaging (SPEBI) [Refs. 10, 14-16]. In this technique, the full (amplitude and phase) spectrum of the medium is obtained, by direct measurement of the amplitude spectrum and the derivative of the phase spectrum. The phase spectrum is then calculated by integrating the phase-derivative spectrum. The phase-derivative spectrum is much easier to measure than the actual phase spectrum, as disclosed in the prior art, since it is significantly simpler than direct phase-measuring techniques such as interferometry or ellipsometry. For example, for a source in the optical regime, it is done by modulating the light source at an RF frequency, e.g. 1 GHz, illuminating the medium, detecting the reflected or transmitted light, and then measuring the RF phase lag of the detected light with respect to the illuminating light. The phase lag divided by the modulation frequency is approximately the phase derivative at the carrier frequency of the light. By carrying out this measurement over a set of frequencies within the spectral range of interest, and then integrating the result, the phase spectrum of the medium is obtained. This gives the complete spectrum of the medium, and completely characterizes its' optical properties. If it is desired to obtain a 'ballistic' image of the medium, it can now be computed by carrying out an inverse Fourier transform on the complex (amplitude and phase) spectrum, to obtain the optical impulse response of the medium, as explained above.

The SPEBI technique, although proven to be very accurate, has a serious drawback: the phase derivative must be measured for many optical carrier frequencies. Depending upon the application, performing the required number of measurements can be too time-consuming. On the other hand, the KK technique relies on amplitude measurements which are inherently fast, and it has been shown above in the review of the prior art that it can be used to derive the impulse response of a diffuse medium, however it may be less accurate than SPEBI. As described above, phase-anchoring techniques can be employed to improve the accuracy of KK, but phase measurements are difficult and susceptible to noise.

Another technique known to be useful for determining the phase spectrum from amplitude measurements is based upon the maximum entropy model (MEM). The MEM technique is described in Ref. [3] and other references therein. However, as in the case of the KK method, its' implementation for diffuse media has not been disclosed or demonstrated in the past. The power spectrum $|H(\omega)|^2$ is measured in a finite spectral range $\omega_L \leq \omega \leq \omega_H$, and then this spectrum is fitted to the MEM model, given by $$|H(v)|^2 = \frac{|\beta|^2}{|A_M(v)|^2} \qquad (9)$$

where $A_M(v) = 1 + \Sigma_{m=1}^M \alpha_m \exp(-i2\pi m v)$ is a MEM polynomial given by the MEM coefficients $\alpha_m$ and by the normalized frequency $v \equiv (\omega - \omega_L)/(\omega_H - \omega_L)$. The unknown coefficients $\alpha_m$ and $|\beta|^2$ are obtained by the system of equations:

$$\begin{pmatrix} C(0) & C(-1) & \cdots & C(-M) \\ C(1) & C(0) & \cdots & C(1-M) \\ \vdots & \vdots & \ddots & \vdots \\ C(M) & C(M-1) & \cdots & C(0) \end{pmatrix} \begin{pmatrix} 1 \\ a_1 \\ \vdots \\ a_M \end{pmatrix} = \begin{pmatrix} |\beta|^2 \\ 0 \\ \vdots \\ 0 \end{pmatrix} \qquad (10)$$

where $C(t) = \int_0^1 |H(v)|^2 \exp(i2\pi t v) dv$ is an autocorrelation function. As in the KK technique, it is desired to calculate the true complex spectrum $$H(v) = |H(v)| \exp(i\theta(v)) = \frac{|\beta| \exp(i\theta(v))}{|A_M(v)|}. \qquad (11)$$

However, due to inaccuracies inherent in the MEM technique, the complex polynomial $A_M(v)$ will have an error in the phase spectrum, i.e. $A_M(v) = |A_M(v)| \exp(i\psi(v))$ instead of the true $A_M(v) = |A_M(v)| \exp(-i\theta(v))$, Therefore, the error phase spectrum $$\phi(v) = \theta(v) - \psi(v) \qquad (12)$$

must be determined in order to determine the true spectrum $\theta(v)$.

SUMMARY OF THE INVENTION

Some embodiments of the invention provide methods and devices for acquiring the phase spectrum of a medium, in some embodiments the electromagnetic phase spectrum, which in some embodiments overcome disadvantages of the prior art.

Some embodiments of the invention provide a robust and fast technique for obtaining an accurate phase spectrum, by measuring the phase derivative at certain frequencies.

Some embodiments of the invention utilize the amplitude and phase spectrum, for imaging through scattering media, detecting objects within the scattering medium or for spectral characterization of any medium.

An aspect of some embodiments of the invention is a method for determining the phase spectrum of the complex spectral transfer function of a medium. The method comprise: determining the derivative of the phase spectrum, i.e. the phase-derivative spectrum, from the measured amplitude of the spectral transfer function; and integrating the phase-derivative spectrum to acquire the phase spectrum.

The phase spectrum can be derived from a known amplitude spectrum, e.g. the Kramers-Kronig (KK) relation or the maximum entropy model (MEM), using any phase-retrieval procedure. According to some embodiments of the invention the phase spectrum is at least partially measured directly.

In some embodiments of the invention, the phase derivative spectrum is determined from the amplitude of the spectral transfer function by measuring the phase-derivative at one or more frequencies and using the measured phase derivatives to reconstruct the phase-derivative spectrum for all frequencies in the spectral range.

Embodiments of the invention can be applied to a medium or an object that is a diffusive (scattering) medium that at least partially scatters the radiation in a diffuse manner. Thus, some embodiments allow for detection and imaging of objects embedded within the diffusive medium. The objects can be selected from the group comprising: abnormalities and/or other physiological conditions of biological tissue; cancerous growth; any sub-surface tissue structure; optical elements or devices; semiconductor elements or devices; objects within fog, water, clouds, or smoke; and objects concealed behind clothing.

According to some embodiments, a method of determining the phase derivative spectrum from the amplitude of the spectral transfer function comprises:
 a. providing a radiation source adapted to produce an beam (in some embodiments, a beam of electromagnetic radiation) having a wide spectral width;
 b. using a modulator controlled by electrical signals from a signal generator to modulate the beam;
 c. causing the modulated beam to interact with the medium;
 d. using an arrangement adapted for collecting radiation to collect radiation that has interacted with the medium;
 e. using a beam divider to divide the collected radiation into two portions;
 f. using a device adapted to measure the intensity of radiation having different spectral components to measure the amplitude spectrum of the first portion of the collected radiation;
 g. transferring the measured intensity spectrum to a computer;
 h. using a device adapted to divide a beam of radiation into its spectral components to divide the second portion of the collected radiation;
 i. using one or more detectors to detect the spectral components of the second portion of collected radiation;
 j. using one or more phase detectors to measure the phase lags of the electrical signals from the one or more detectors relative to the electrical signals from the signal generator;
 k. transferring the measured phase lags to the computer; and
 l. supplying the measured amplitude spectrum and the measured phase lags as inputs to software, which is adapted to run on the computer and to determine the phase spectrum of the medium from the inputs.

The radiation that is collected by the arrangement can be either transmitted through the medium or reflected from the medium.

According to some embodiments, the phase spectrum of the medium is determined by the steps of substituting the measured amplitudes and the measured phase lags in a DMSKK formula (see below) to compute the phase differences and performing a summation of the phase differences.

According to some embodiments, the phase spectrum of the medium is determined by the steps of substituting the measured amplitudes and the measured phase lags in the MEM formula (see below) to compute the error-phase derivatives at the anchoring points, computing a polynomial interpolating function from the error-phase derivatives, determining the error phase spectrum by integrating the polynomial interpolating function, and determining the full complex phase spectrum from the error phase spectrum.

According to an aspect of some embodiments of the invention is a system suitable for carrying out embodiments of the method described above, the system comprising:
 a. a radiation source emitting a beam having a wide spectral width;
 b. a modulator that modulates the beam;
 c. a signal generator producing electrical signals to control the modulator;
 d. an arrangement adapted to collect radiation from the beam after it has interacted with the medium;
 e. a beam divider adapted to divide the collected radiation into two portions;
 f. a device adapted to measure the amplitude spectrum of the first portion of the collected radiation;
 g. a device adapted to split the radiation of the second portion of the collected radiation into its spectral components;
 h. one or more detectors to detect the spectral components of the radiation of the second portion and to convert the detected optical signals into electrical signals;
 i. one or more phase detectors adapted to measure the phase lags of the electrical signals from the one or more detectors relative to the electrical signals produced by the signal generator; and
 j. a computer comprising software that allows the determination of the phase spectrum of the medium from the amplitude spectrum and the phase lags.

The radiation collected by the arrangement can be transmitted through the medium or reflected from the medium.

Some embodiments of the invention relate for determining an phase spectrum $\theta(\omega)$ (in some embodiments the electromagnetic phase spectrum) of the complex spectral transfer function $H(\omega)$ of a medium, where $\ln[H(\omega)] = \ln(|H(\omega)|) + i\theta(\omega)$. In some embodiments, the approximation is used for detecting an object screened by a volume of a scattering medium. In some embodiments, the approximation is used for determining a refractive index spectrum of a volume of an object. In some embodiments, a device that uses the approximation, for example for detecting objects, for imaging objects, and for determining a refractive index spectrum of a volume of material is provided.

In some embodiments, an (in some embodiments, electromagnetic) amplitude spectrum $|H(\omega)|$ of a complex spectral transfer function $H(\omega)$ of a volume of an object is acquired, the nth derivative (n an integer greater than or equal to 0) of the phase spectrum $d^n\theta(\omega)/d\omega^n$ of the complex spectral transfer function $H(\omega)$ is determined from the acquired amplitude spectrum $|H(\omega)|$; and $d^n\theta(\omega)/d\omega^n$ is integrated n times to acquire an phase spectrum $\theta(\omega)$ of the complex spectral transfer function $H(\omega)$.

Thus according to an aspect of some embodiments of the present invention there is provided a method for determining an (in some embodiments, electromagnetic) phase spectrum $\theta(\omega)$ of the complex spectral transfer function $H(\omega)$ of a volume of an object, where $\ln[H(\omega)]=\ln(|H(\omega)|)+i\theta(\omega)$, the method comprising:

a. acquiring an (in some embodiments, electromagnetic) amplitude spectrum $|H(\omega)|$ of a complex spectral transfer function $H(\omega)$ of a volume of an object;

b. determining an nth derivative of the phase spectrum $d^n\theta(\omega)/d\omega^n$ of the complex spectral transfer function $H(\omega)$, from the acquired amplitude spectrum $|H(\omega)|$; and c. integrating the $d^n\theta(\omega)/d\omega^n$ times to acquire an phase spectrum $\theta(\omega)$ of the complex spectral transfer function, wherein n is an integer of at least 0.

In some embodiments, the object scatters radiation (of wavelengths comprising $|H(\omega)|$) and n is an integer of at least 0, e.g., 0, 1, 2, 3 and even greater. In some embodiments, the object scatters or does not-scatter radiation and n is an integer of at least 1, e.g., 1, 2, 3 and even greater.

In some embodiments, n is 1 and the nth derivative is a first derivative. In some embodiments, n is 2 and the nth derivative is a second derivative. In some embodiments, n is 3 and the nth derivative is a third derivative.

In some embodiments, the nth derivative of the phase spectrum $d^n\theta(\omega)/d\omega^n$ is determined by:

calculating an nth derivative $d^n|H(\omega)|/d\omega^n$ of the acquired amplitude spectrum $|H(\omega)|$; and applying a phase-retrieval procedure on $d^n|H(\omega)|/d\omega^n$, thereby determining $d^n\theta(\omega)/d\omega^n$.

In some embodiments, the nth derivative of the phase spectrum $d^n\theta(\omega)/d\omega^n$ is determined by:

calculating an nth derivative $d^n\ln(|H(\omega)|)/d\omega^n$ of the acquired amplitude spectrum $|H(\omega)|$; and applying a phase-retrieval procedure on the $d^n\ln(H(\omega))/d\omega^n$, thereby determining $d^n\theta(\omega)/d\omega^n$. In some embodiments, the phase-retrieval procedure is the Kramers-Kronig (KK) relation. In some embodiments, the phase-retrieval procedure is the maximum entropy method (MEM) technique.

It has been found that in some embodiments, the phase spectrum $\theta(\omega)$ of the complex spectral transfer function $H(\omega)$ of the medium is more accurate than prior methods. It has been found that some embodiments provide superior performances over the prior art Kramers-Kronig relations when applied on a finite spectral width. Using some embodiments, divergences at the spectrum boundaries are milder and the time-delay is more accurate throughout the spectral range. At derivatives higher than the first derivative, results are improved even more.

Some embodiments provide for faster or more accurate acquisition of the phase spectrum of a medium.

In some embodiments, spectral properties of the material are determined. In some embodiments, an object screened by the medium (especially a scattering medium) is detected or an image of the object is acquired.

Thus, according to an aspect of some embodiments of the invention there is provided a method for detecting (and even imaging) an object screened by a volume of a scattering medium, comprising:

a) providing a transmitter;

b) projecting a beam of radiation from the transmitter to interact with a volume of a scattering medium;

c) using a detector to acquire an (in some embodiments, electromagnetic) amplitude spectrum $|H(\omega)|$ of a complex spectral transfer function $H(\omega)$, where $\ln[H(\omega)]=\ln(|H(\omega)|)+i\theta(\omega)$, of the volume of the medium;

d) determining an phase spectrum $\theta(\omega)$ of the complex spectral transfer function $H(\omega)$ of the volume, for example substantially as described herein;

e) calculating the complex spectral transfer function $H(\omega)$ of the volume from the acquired amplitude spectrum $|H(\omega)|$ and the determined phase spectrum $\theta(\omega)$;

f) converting the calculated $H(\omega)$ to the impulse response $h(t)$ of the volume; and g) if an object is screened by the volume of the medium, detecting the object.

According to an aspect of some embodiments of the invention there is also provided a method for determining a refractive index spectrum of a volume of an object, comprising:

a) providing a transmitter;

b) projecting a beam of radiation from the transmitter to interact with a volume of an object;

c) using a detector to acquire an (in some embodiments, electromagnetic) amplitude spectrum $|H(\omega)|$ of a complex spectral transfer function $H(\omega)$ of the volume, where $\ln[H(\omega)]=\ln(|H(\omega)|)+i\theta(\omega)$;

d) determining an phase spectrum $\theta(\omega)$ of the complex spectral transfer function $H(\omega)$, for example, substantially as described herein; and e) calculating the complex spectral transfer function $H(\omega)$ of the volume from the acquired amplitude spectrum $|H(\omega)|$ and the determined phase spectrum $\theta(\omega)$;

thereby determining a refractive index spectrum (which is the complex spectral transfer function $H(\omega)$) of the volume of the object.

According to an aspect of some embodiments of the invention there is also provided a device suitable for determining an (in some embodiments, electromagnetic) phase spectrum $\theta(\omega)$ of the complex spectral transfer function $H(\omega)$ of a volume of an object, for example for implementing methods of the invention such as described above, comprising:

a) a transmitter, configured to project a beam of radiation at a volume of an object of interest;

b) a detector configured to acquire the radiation projected by the transmitter subsequent to interaction with the volume and to output an (in some embodiments, electromagnetic) amplitude spectrum $|H(\omega)|$ of the acquired radiation; and c) a signal analysis assembly functionally associated with the detector, configured to:

obtain the amplitude spectrum $|H(\omega)|$ from the detector; and calculate an phase spectrum $\theta(\omega)$ of the complex spectral transfer function $H(\omega)$, where $\ln[H(\omega)]=\ln(|H(\omega)|)+i\theta(\omega)$, of the volume from the amplitude spectrum $|H(\omega)|$, for example as described herein.

All the above and other characteristics and advantages of the invention will be further understood through the following illustrative and non-limitative description of preferred embodiments thereof, with reference to the appended drawings.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

As used herein, the indefinite articles "a" and "an" mean "at least one" or "one or more" unless the context clearly dictates otherwise.

Herein, by scattering medium or diffusive medium is meant a medium that radiation passing through the medium is forced to deviate from a straight path by a plurality of localized non-uniformities in the medium so that the radiation is scattered.

Herein, the terms "medium" and "object" are sometimes used interchangeably. In some instances, the teachings of the invention are applied to study, detect or image an object, which in some instances screened by a medium. The meaning of these terms is clear from the specific context in which used.

Herein, the terms "system" and "device" are sometimes used interchangeably. The meaning of these terms is clear from the specific context in which used.

BRIEF DESCRIPTION OF THE FIGURES

Some embodiments of the invention are herein described, by way of example only, with reference to the accompanying figures. The description, together with the figures, makes apparent how embodiments of the invention may be practiced to a person having ordinary skill in the art. The figures are for the purpose of illustrative discussion of embodiments of the invention and no attempt is made to show structural details of an embodiment in more detail than is necessary for a fundamental understanding of the invention. For the sake of clarity, some objects depicted in the figures are not to scale.

DETAILED DESCRIPTION OF SOME EMBODIMENTS OF THE INVENTION

Figure 1:
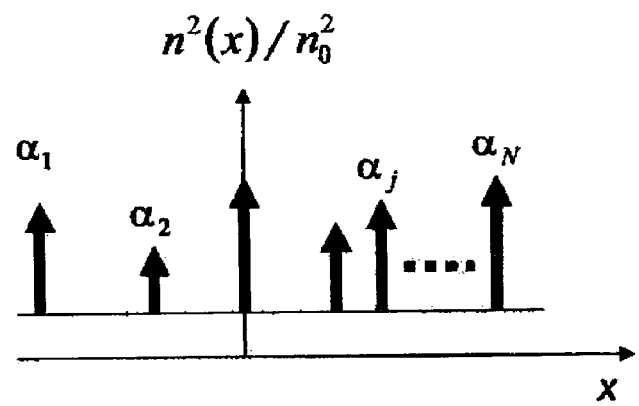
FIG. 1 is a schematic presentation of a model of a diffusive medium in which each scatterer is a delta function change in the refractive index.

Some embodiments of the present invention provide new methods of acquiring the phase spectrum of a medium, which are, in some embodiments, accurate, fast and robust. Some embodiments do not require direct phase measurements such as interferometric or ellipsometric measurements. Some embodiments are very accurate even for a relatively narrow spectrum of measurements. Some embodiments allow for the accurate determination of a full complex spectrum from straightforward transmission or reflection intensity measurements. In another aspect the invention provides a system that allows the method to be carried out.

According to an aspect of some embodiments of the invention an derivative $d^n\theta(\omega)/d\omega^n$ of phase spectrum $\theta(\omega)$ of the complex spectral transfer function $H(\omega)$ is determined, and then the phase spectrum $\theta(\omega)$ acquired by integration of the derivative.

In some embodiments, for convenience call DMSKK, $d\theta(\omega)/d\omega$ is determined using the Kramers-Kronig relation together with SPEBI.

In some embodiments $d\theta(\omega)/\omega$ is determined using the maximum entropy method (MEM) technique together with SPEBI.

In some embodiments, for convenience call DKK, $d\theta(\omega)/d\omega$ is determined by applying the Kramers-Kronig relation to the derivative of the amplitude spectrum $|H(\omega)|$ of a complex spectral transfer function $H(\omega)$, which can be used alone or together with SPEBI.

In some embodiments, the determined phase spectrum $\theta(\omega)$ of the complex spectral transfer function $H(\omega)$ is used for detecting objects or acquiring images of objects, for example of objects screened by a scattering medium.

In some embodiments, the determined phase spectrum $\theta(\omega)$ of the complex spectral transfer function $H(\omega)$ is used for determining a refractive index spectrum of a volume of an object.

DMSKK: Kramers-Kronig with SPEBI

A embodiment of the invention integrates the Kramers-Kronig (KK) and Spectral Ballistic Imaging (SPEBI) techniques (Refs. 10, 14-16). That is, instead of measuring the phase directly, the phase-difference $\Delta\theta$ is measured for one or more "anchoring" frequencies. These measurements are then used to reconstruct the phase-derivative spectrum $$\frac{d\theta(\omega)}{d\omega}$$

for all frequencies in the spectral range, from which the phase spectrum is then easily acquired through integration.

Therefore, the present invention provides a way of implementing the KK technique to acquire an accurate phase-derivative spectrum, together with a way of anchoring the phase-derivative spectrum. By taking the derivative of eq. (2), we get:

$$\frac{d\ln[H(\omega)]}{d\omega} = \frac{d\ln|H(\omega)|}{d\omega} + i\frac{d\theta(\omega)}{d\omega} \quad (13)$$

whose real and imaginary parts are connected through the KK relations. The phase-derivative spectrum can be anchored through a new method disclosed herein, which is called by the inventors the differential multiply-subtractive Kramers-Kronig method (DMSKK), and can be written $$\frac{\theta'(\omega)}{\omega} = \frac{\theta'(\omega_1)}{\omega_1} \frac{(\omega^2 - \omega_2^2)(\omega^2 - \omega_3^2) \ldots (\omega^2 - \omega_Q^2)}{(\omega_1^2 - \omega_2^2)(\omega_1^2 - \omega_3^2) \ldots (\omega_1^2 - \omega_Q^2)} +$$
$$\ldots \frac{\theta'(\omega_j)}{\omega_j} \frac{(\omega^2 - \omega_1^2) \ldots (\omega^2 - \omega_{j-1}^2)(\omega^2 - \omega_{j+1}^2) \ldots (\omega^2 - \omega_Q^2)}{(\omega_j^2 - \omega_1^2) \ldots (\omega_j^2 - \omega_{j-1}^2)(\omega_j^2 - \omega_{j+1}^2) \ldots (\omega_j^2 - \omega_Q^2)} +$$
$$\ldots \frac{\theta'(\omega_Q)}{\omega_Q} \frac{(\omega^2 - \omega_1^2)(\omega^2 - \omega_2^2) \ldots (\omega^2 - \omega_{Q-1}^2)}{(\omega_Q^2 - \omega_1^2)(\omega_Q^2 - \omega_2^2) \ldots (\omega_Q^2 - \omega_{Q-1}^2)} -$$
$$\frac{2}{\pi}(\omega^2 - \omega_1^2)(\omega^2 - \omega_2^2) \ldots (\omega^2 - \omega_Q^2) P$$
$$\int_0^\infty \frac{\ln|H(\varpi)|/d\varpi|_{\varpi=\omega'}}{(\omega'^2 - \omega^2)(\omega'^2 - \omega_1^2) \ldots (\omega'^2 - \omega_Q^2)} d\omega' \quad (14)$$

or, in a more compact form $$\frac{\theta'(\omega)}{\omega} = \sum_{j=1}^{Q} \frac{\theta'(\omega_j)}{\omega_j} \prod_{n=1\neq j}^{Q} \frac{(\omega^2 - \omega_n^2)}{(\omega_j^2 - \omega_n^2)} -$$
$$\frac{2}{\pi}\prod_{n=1}^{Q}(\omega^2 - \omega_n^2) P \int_0^\infty \frac{d\ln|H(\varpi)|/d\varpi|_{\varpi=\omega'}}{(\omega'^2 - \omega^2)\prod_{n=1}^{Q}(\omega'^2 - \omega_n^2)} d\omega' \quad (15)$$

where,
$\theta'(\omega_j) \equiv d\theta(\overline{\omega})/d\overline{\omega}|_{\overline{\omega}=\omega_j}$ and Q is the number of frequency "anchoring" points for which the phase-derivative values are directly measured.

It is to be noted that a novel feature of the above is the fact that the form of eq. (13) lends itself to a KK analysis of the phase derivative spectrum, which is the imaginary part of the function, by knowledge of the real part of the function, which is the derivative of the natural log of the amplitude spectrum. The knowledge of the real part is acquired by direct measurements of the amplitude spectrum with the use of a spectrometer, monochromator, or other suitable instruments known in the art. This has not been previously appreciated, since previous work focused on the phase spectrum itself and not on the phase-derivative spectrum. Therefore there was no need to work with the derivative of eq. (2). This new approach leads to Eq. (15), which is a new method of anchoring the phase-derivative that has not been disclosed in the prior art.

In practice, the amplitude is measured only for a finite number of frequencies M, i.e., if the differences between two adjacent frequencies is $\Delta\omega$ then $M=(\omega_H-\omega_L)/\Delta\omega$ (obviously, M>>Q, otherwise there will be no motivation to use the DMSKK method). Since what is actually measured in the SPEBI technique is the phase difference between two closely-spaced frequency sidebands (and not directly the derivative) and since the spectral range is finite, the DMSKK can be written $$\frac{\Delta\theta(\omega)}{\omega} = \sum_{j=1}^{Q} \frac{\Delta\theta(\omega_j)}{\omega_j} \prod_{n=1\neq j}^{Q} \frac{(\omega^2 - \omega_n^2)}{(\omega_j^2 - \omega_n^2)} -$$
$$\frac{2}{\pi}\prod_{n=1}^{Q}(\omega^2 - \omega_n^2) \sum_m{}' \frac{\Delta\ln|H(\omega_m)|}{(\omega_m^2 - \omega^2)\prod_{n=1}^{Q}(\omega_m^2 - \omega_n^2)} \Delta\omega \quad (16)$$

where $\Sigma_m'$ stands for summation over all the frequencies in the spectral range, i.e.

$$\omega_m = \omega_L + (m-1)\Delta\omega \quad (17)$$

but excludes the frequencies of the poles $\omega_n$, i.e. the Q 'anchor' frequencies for which the phase difference is given. $\Delta\theta(\omega_i)$ and $\Delta \ln |H(\omega_i)|$ are the experimentally measured difference in phase and difference in ln $|H(\omega_i)|$ respectively, for two closely-spaced frequency sidebands around frequency $\omega_i$, and $\Delta\omega$ is the difference in frequency between the sidebands, as the SPEBI experimental technique dictates.

For completeness, in the case where only one phase difference is given, $$\frac{\Delta\theta(\omega)}{\omega} = \frac{\Delta\theta(\omega_1)}{\omega_1} - \frac{2}{\pi}(\omega^2 - \omega_1^2)\sum_m{}' \frac{\Delta\ln|H(\omega_m)|}{(\omega_m^2 - \omega^2)(\omega_m^2 - \omega_1^2)} \Delta\omega. \quad (18)$$

The phase difference spectrum $\Delta\theta(\omega)$ can then be evaluated from equations (16) (or (18)) for any $\omega$. From this, the phase $\theta(\omega)$ can easily be retrieved by using the SPEBI formalism [Refs. 10, 14-16]

$$\theta(\omega_m) = \sum_{j=1}^{m} \Delta\theta(\omega_j). \quad (19)$$

This DMSKK method was checked by simulating a 1D homogenous medium with N delta function scatterers randomly distributed in the medium each having a different strength, i.e. a different refractive index and width, as depicted in FIG. 1. A delta function scatterer represents a scatterer whose width $l_j$ is considerably smaller than the source's wavelength $\lambda$ (i.e., $l_j<<\lambda$ for every j). For simplicity polarization effects are ignored. Thus the 1D stationary-state wave equation has the form $$\frac{\partial^2}{\partial x^2}\psi^2 + \left(\frac{2\pi n(x)}{\lambda}\right)^2 \psi = 0 \quad (20)$$

where $\psi(x)$ is the electromagnetic field and $n(x)$ is the refractive index.

Using the definition of the wavenumber $k \equiv 2\pi n_0/\lambda$ the wave equation can be written $$\frac{\partial^2}{\partial x^2}\psi + k^2\left(1 + 2\frac{\Delta n(x)}{n_0}\right)\psi = 0, \quad (21)$$

where:

$$2\Delta n(x)/n_0 = \sum_{j=1}^{N} \alpha_j \delta(x - L_j);$$

N is the number of scatterers;

$$L_j = L_{j-1}a_j = \sum_{m=1}^{j} a_m$$

is the position of the jth scatterer, i.e. $\alpha_j$ are the distances between two adjacent scatterers; and $$\alpha_j = 2\frac{\delta n_j l_j}{n_0} \quad (22)$$

is the strength of the jth scatterer. $\delta n_j$ and $l_j$ are the change in its refractive index and its size respectively.
Therefore, the wave equation for the diffusive medium reads $$\frac{\partial^2}{\partial x^2}\psi + k^2\left[1 + \sum_{j=1}^{N} \alpha_j \delta(x - L_j)\right]\psi = 0. \quad (23)$$

The use of delta function scatterers is just an example of a complex medium. In fact, any medium, diffuse or otherwise, could be chosen for the purpose of demonstrating a method of the invention. The motivation for using this specific medium and the solution of Eq. (23) are given in ref. 4 and will not be included herein.

The simulation was carried out using similar parameters to those used in Ref 4. That is: $n_0=1$ and $N=1000$ point scatterers, where the distance between them is a random variable, distributed uniformly between 0 and 5 μm, i.e. $0 \leq \alpha_j \leq 5$ μm. The strength of each scatterer is also a uniform random number so that $0 \leq \alpha_j \leq 0.03$ μm This corresponds to glass particles having widths on the order of tens of nanometers. The spectral range was $2\pi \times 300$ THz $\leq \omega \leq 2\pi \times 301.2$ THz, so that the spectral width was 1.2 THz. The spectral resolution was $\Delta\omega = \Omega = 2\pi \times 3$ GHz, i.e., 400 "measurements" were taken.

Figure 2A:
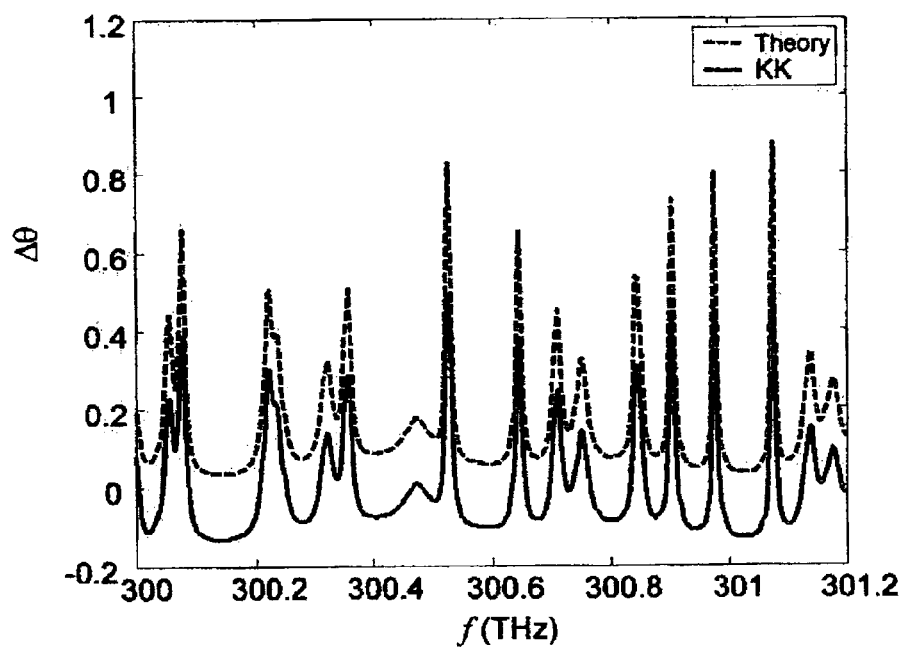
FIG. 2A displays the comparison between theoretical phase difference spectrum $\Delta\theta$ and a reconstruction of $\Delta\theta$ using the KK method.
Figure 2B:
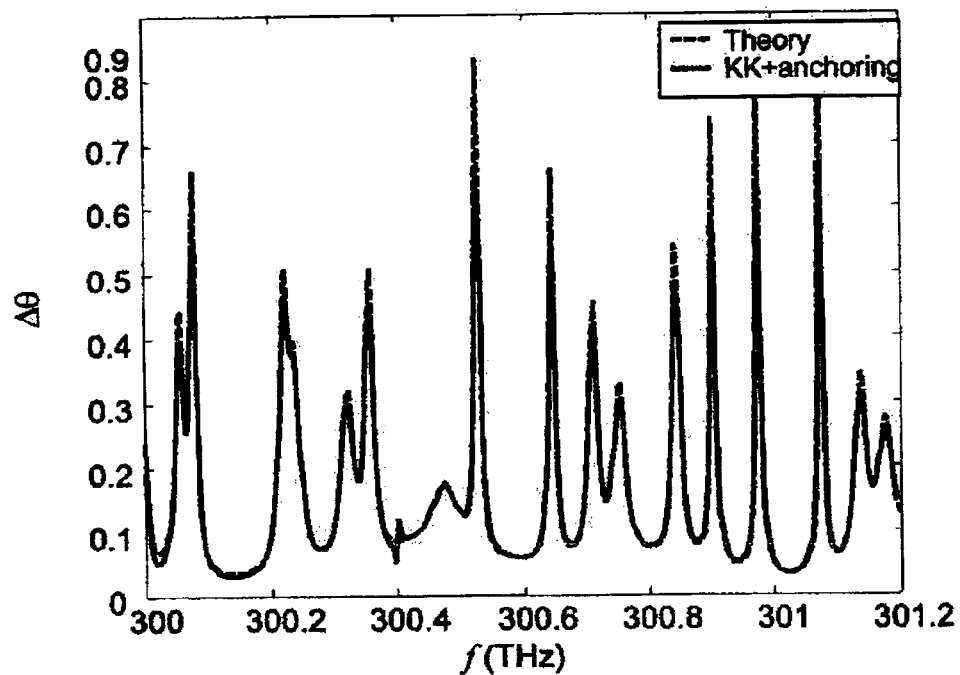
FIG. 2B displays the comparison between theoretical $\Delta\theta$ and a reconstruction of $\Delta\theta$ using the KK with anchoring method.
Figure 2C:
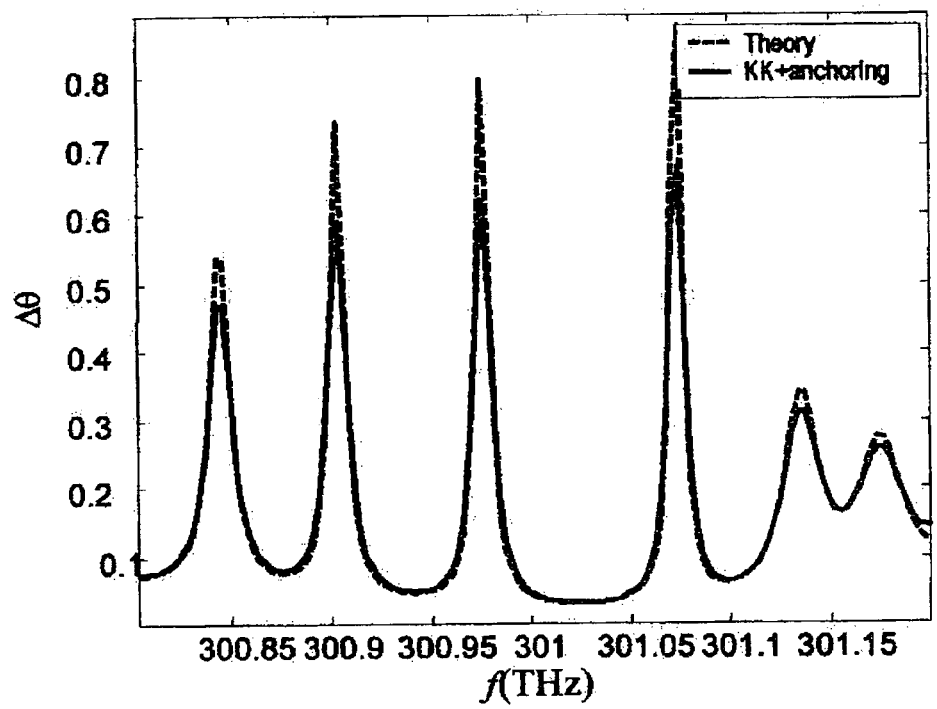
FIG. 2C is a zoom-in of apportion of FIG. 2B.

FIG. 2A displays the comparison of the exact $\Delta\theta$ spectrum of the above model (dashed line) to the KK-derived $\Delta\theta$ spectrum (solid line), FIG. 2B compares the exact $\Delta\theta$ spectrum (dashed line) to the KK-derived spectrum with phase-derivative anchoring using the disclosed DMSKK relation of the invention (solid line), and FIG. 2C is an enlarged view of a portion of FIG. 2B centered at ~f=301 THz. For the DMSKK method the anchoring point used was $\omega_1=2\pi \times 300.4$ THz. As can be seen, the prior art KK relation has two main problems that are easily discerned from the graphs of FIG. 2A. The first problem is that there is a phase shift between the KK result and theoretical value. The second problem is that the KK method fails at the boundaries of the spectral range. On the other hand, the DMSKK method of the invention yields superior performance without the need to measure the phase directly.

MEM with SPEBI

Some embodiments of the invention integrate the MEM technique (Ref. 3) with the SPEBI technique, in order to improve the accuracy of the MEM-derived phase spectrum. This is done by directly measuring L phase derivative values $\theta'(v_l)$ of the true phase $\theta(v)$ using the SPEBI technique at "anchoring" frequencies $v_l$, where $1 \leq l \leq L$. As was explained above for the KK technique, this measurement is much simpler then a direct measurement of optical phase at the desired anchoring frequencies. Taking the derivative of eq. (12), we get $$\phi'(v) = \theta'(v) - \psi'(v) \quad (24)$$

which allows us to determine L values of the error-phase derivative from the L measured values of $\theta'(v)$ and the MEM-derived $\psi(v)$ via:

$$\phi'(v_l) = \theta'(v_l) - \psi'(v_l). \quad (25)$$

From these L values of the derivative of the error phase, a polynomial interpolating function can be determined to estimate $\phi'(v)$:

$$\phi'(v) \cong E_0 + E_1 v + \ldots + E_L v^L = \sum_{l=0}^{L} E_l v^l \quad (26)$$

and then the error phase spectrum $\phi(v)$ can be determined by integrating eq. (26). Finally, the desired phase spectrum $\theta(v)$ is calculated from eq. (12).

Figure 3A:
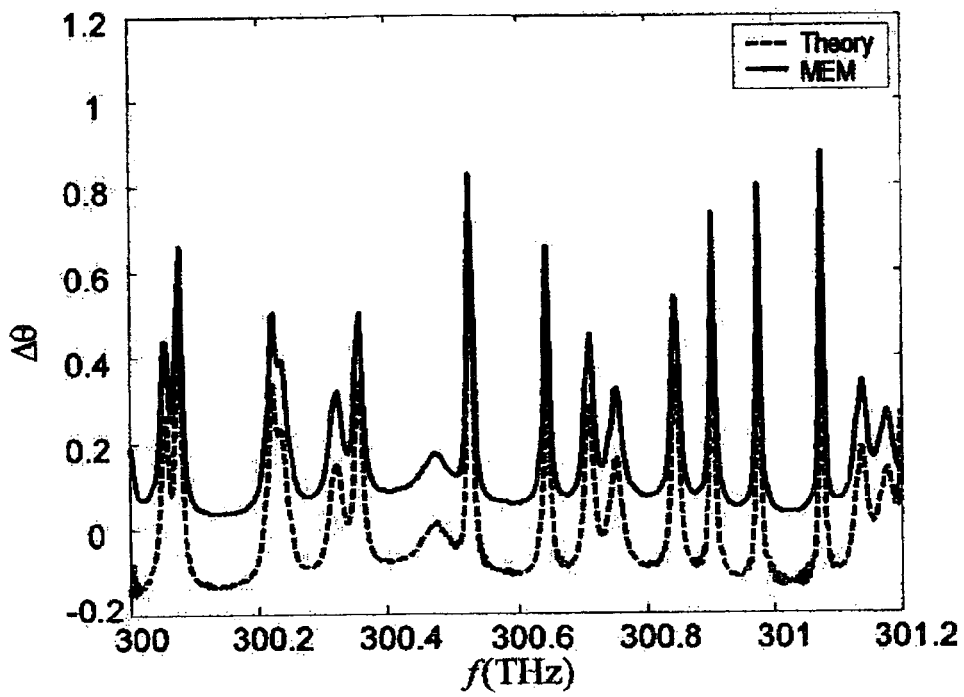
FIG. 3A displays the comparison between theoretical $\Delta\theta$ and a reconstruction of $\Delta\theta$ using the MEM method.
Figure 3B:
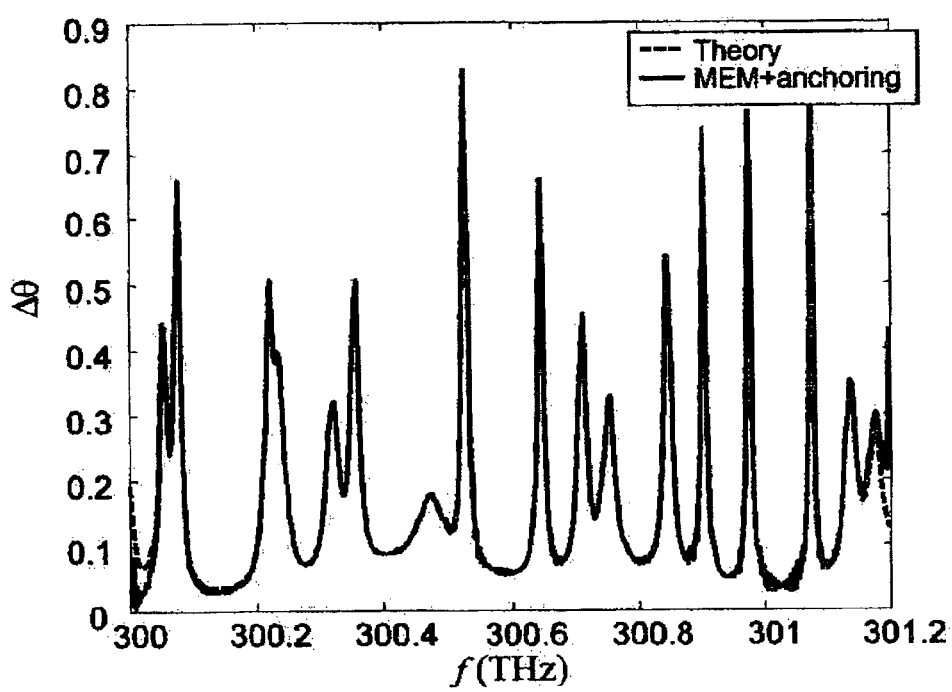
FIG. 3B displays the comparison between theoretical $\Delta\theta$ and a reconstruction of $\Delta\theta$ using the MEM with anchoring method.
Figure 3C:
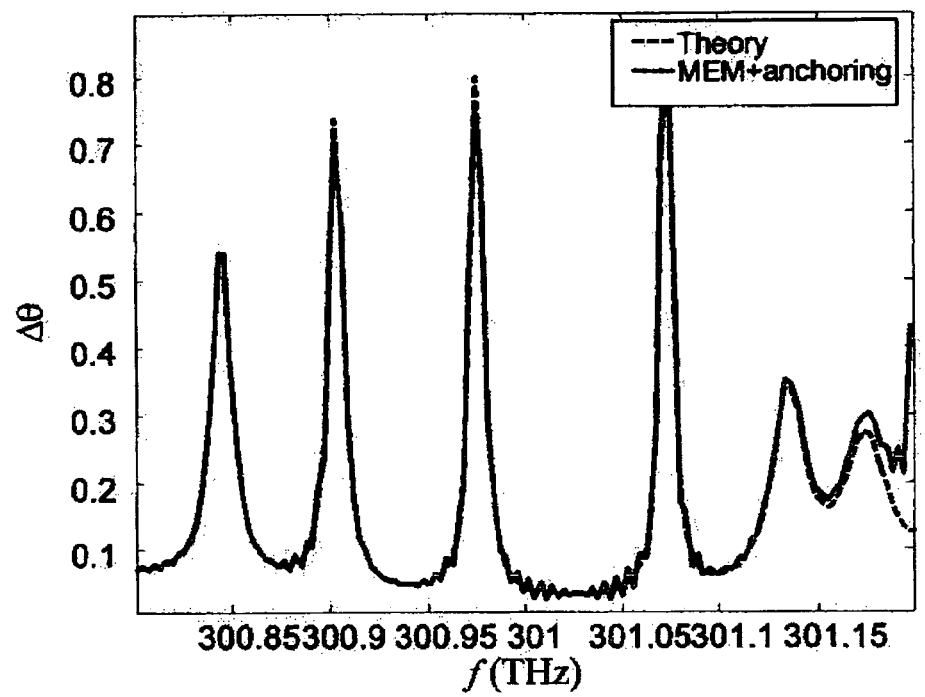
FIG. 3C is similar to FIG. 3B but when the reconstruction was done for a narrower spectrum.

Using the same model of 1000 scatterers described above (after eq. 19), this method for phase-derivative anchoring in the MEM technique was checked. FIGS. 3A and 3B display a comparison between theoretical phase-difference spectrum and the MEM result with (FIG. 3B) and without (FIG. 3A) the anchoring method. FIG. 3C is an enlarged view of a portion of FIG. 3B centered at ~f=301 THz. The phase difference $\Delta\theta$ was measured for the frequency interval $\Delta\omega = \Omega = 2\pi \times 3$ GHz. The anchoring frequency was $\omega_1 = 2\pi \times 300.4$ THz. The use of phase-derivative anchoring is seen to significantly improve the accuracy of the spectrum, as compared to the prior art.

As can be understood from the results summarized in FIG. 2A to FIG. 4, the differential phase-anchoring technique of the invention as implemented for example with DMSKK and MEM with SPEBI and as detailed hereinbelow for additional embodiments of the invention, gives improved results for characterizing the spectral qualities of any medium, and/or imaging through a medium that at least partially scatters the radiation in a diffuse manner. Examples of such a medium are: fog, biological tissue, water, and clothing. Imaging using the differential phase-anchoring technique of the invention allows for detection and imaging of objects embedded within the diffusive medium. This can be done, for example, in the same fashion as disclosed in Refs 16 and 4, i.e. inverse-Fourier transform of the amplitude and phase spectrum to compute the electromagnetic impulse-response in the time domain, and then detecting the medium's embedded objects by analyzing the ballistic or quasi-ballistic response, which carries the nearly undistorted information on the image of the embedded objects. The differential phase-anchoring technique of the invention can be used in many practical applications, e.g. detecting and/or imaging abnormalities and physiological state of biological tissue, cancerous growth, any sub-surface tissue structure, and detecting and identifying objects within fog, water, clouds, smoke, or behind clothing.

Figure 4:
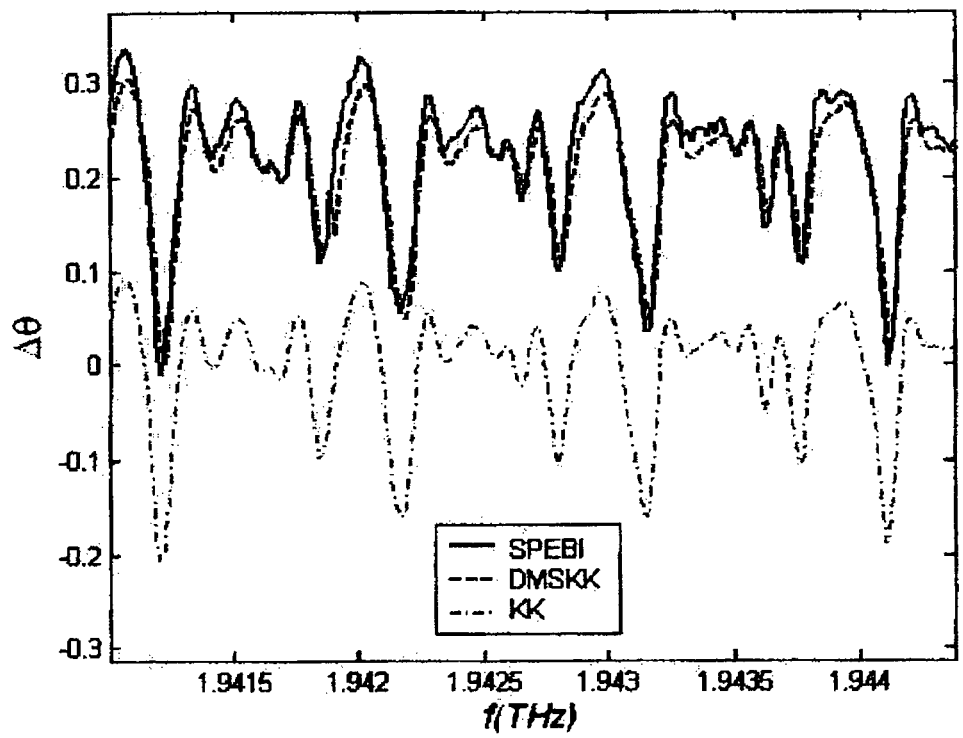
FIG. 4 displays the results of an experiment that shows the comparison between the $\Delta\theta$ spectrum for the SPEBI method, the KK phase-retrieval method, and the DMSKK method.

The above was tested experimentally by taking an optically diffusive medium consisting of 13 glass plates (width 1 mm), which were placed in a random manner. The spectrum of the medium was measured using the SPEBI technique [Refs. 10, 14-16]. In FIG. 4 a comparison between the SPEBI measurement (solid line), the KK derivation of the phase-difference spectrum (dotted-dashed line) and that of the DMSKK derivation (for a single anchoring point, dashed line) is presented. As can be seen from the figure, the DMSKK (where the anchoring frequency was $\omega_1=2\pi\times194.17$ THz) plot is substantially closer to the measured SPEBI results than the KK one.

DKK

In another embodiment, an improved Kramers-Kronig method is described, which the inventors call the Differential Kramers-Kronig (DKK) method. Aspects of this embodiment are discussed further in detail hereinbelow. The DKK results in a phase spectrum having higher accuracy then the well-known Kramers-Kronig derived spectrum $\theta_{KK}(\omega)$ described in eq. (5), even without the need for the DMSKK phase-anchoring method described hereinabove. Starting from eq. (13)

$$\frac{d\ln[H(\omega)]}{d\omega} = \frac{d\ln|H(\omega)|}{d\omega} + i\frac{d\theta}{d\omega} \quad (13)$$

the KK relation between the imaginary and real part gives:

$$\frac{d\theta(\omega)}{d\omega} = \frac{1}{\pi}P\int_0^\infty \frac{2\omega}{\omega^2-\omega'^2}\frac{d}{d\omega'}\ln|H(\omega')|d\omega' \quad (27)$$

where P denotes principle value. After integration this becomes $$\theta(\omega) - \theta(\omega_0) = \frac{2}{\pi}P\int_0^\infty \ln\left(\left|\frac{\omega^2-\omega'^2}{\omega_0^2-\omega'^2}\right|\right)\frac{d}{d\omega'}\ln|H(\omega')|d\omega' \quad (28)$$

In principle, this equation will give the same results as the regular KK relation described in eq. (4), since both assume that the spectrum's amplitude is known over an infinite spectral width. However, in practice this is obviously not possible. Due to the finite spectral width the phase spectrum $\theta_{DKK}(\omega)$ is approximate, and is described by:

$$\theta_{DKK}(\omega) = \theta(\omega_0) + \frac{2}{\pi}P\int_{\omega_L}^{\omega_H} \ln\left(\left|\frac{\omega^2-\omega'^2}{\omega_0^2-\omega'^2}\right|\right)\frac{d}{d\omega'}\ln|H(\omega')|d\omega' \quad (29)$$

Figure 5A:
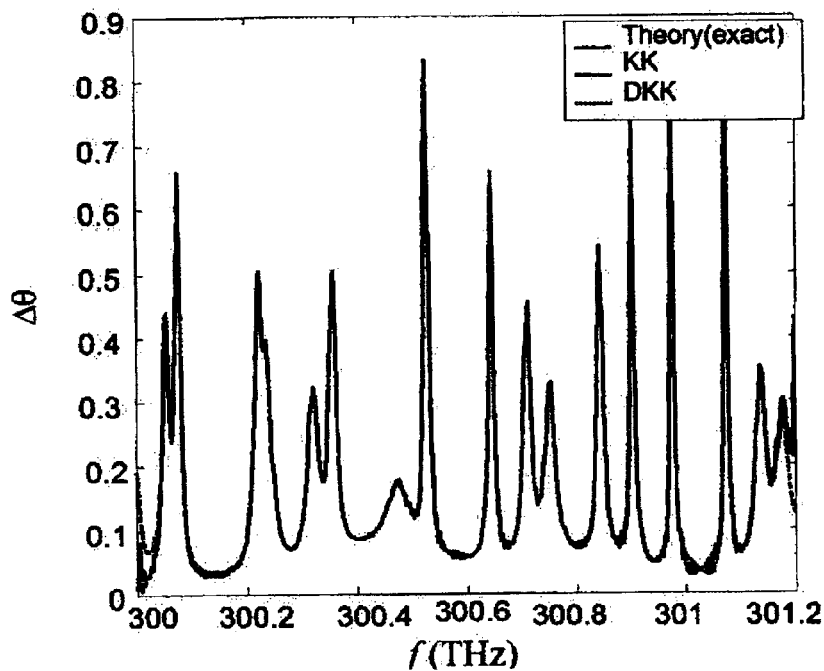
FIG. 5A displays the comparison between theoretical $\Delta\theta$ spectrum, the reconstruction of $\Delta\theta$ using the regular Kramers-Kronig method, and the reconstruction of $\Delta\theta$ using the disclosed "differential Kramers-Kronig" (DKK) method.
Figure 5B:
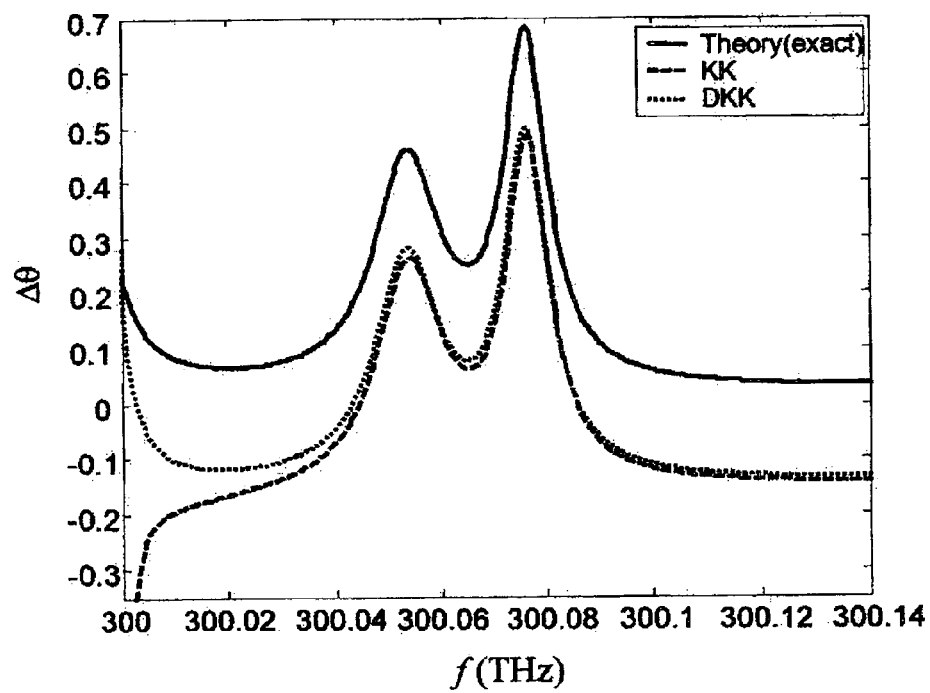
FIG. 5B is a zoom-in of a portion of FIG. 5A.

FIGS. 5A and 5B show that this spectrum has improved accuracy as compared to the regular KK phase spectrum $$\theta_{KK}(\omega) = -\frac{2\omega}{\pi}P\int_{\omega_L}^{\omega_H}\frac{\ln|H(\omega')|}{\omega'^2-\omega^2}d\omega' \quad (4)$$

Using the same simulation of a diffuse medium described herein above, FIG. 5A displays the comparison between theoretical (true) phase-difference spectrum, the reconstruction of the phase-difference spectrum using the regular Kramers-Kronig method [Eq. (4)], and the reconstruction using the disclosed "differential Kramers-Kronig" (DKK) method [Eq. (29)]. FIG. 5B is a zoom-in of a portion of FIG. 5A. It is shown that the use of the DKK method improves the accuracy of the phase spectrum, especially at the boundaries of the spectrum, where the regular KK method fails.

Embodiment of a Practical Implementation

Figure 6:
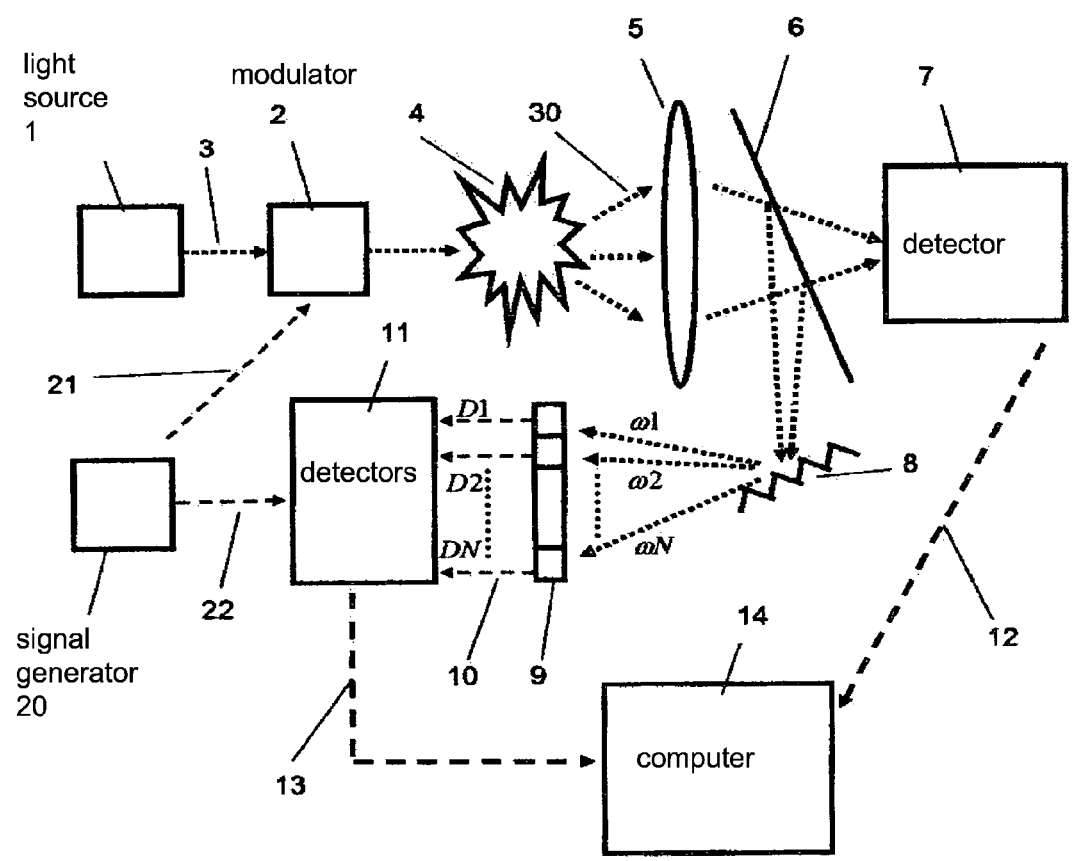
FIG. 6 A schematic illustration of an embodiment of a system.

FIG. 6 schematically shows an embodiment of a system for carrying out the necessary measurements required by some embodiments of the invention which include application of SPEBI. In FIG. 6, dotted arrows denote light paths and dashed arrows denote electronic signal paths. A light source 1 (transmitter) emits a light beam 3, which has a wide spectral width SW whose value is at least $SW=\omega_H-\omega_L$. The light source can be a laser, light emitting diode, or any other electromagnetic source. In some embodiments, the transmitter is a non-electromagnetic source such as an ultrasound transducer. The light is modulated in a modulator 2, which can be any optical modulator known in the art, e.g. electrooptic, acoustooptic, or mechanical chopper. In one preferred embodiment, the modulation is amplitude modulation, i.e. of the form $\cos(\Omega t)$, where $\Omega=2\pi f$ and f is the light modulation frequency in Hz. Typical values of f lie in the regime between 10 MHz and 10 GHz. The modulator is electronically controlled by a signal generator 20 through electrical connection 21.

The modulated light emitted by the modulator illuminates the medium 4 to be characterized. In an embodiment of the invention, the light 30 that is transmitted through the medium is collected with the use of suitable optical arrangement shown collectively as 5, which can consist of lenses, mirrors, optical fibers (array or single fibers) and/or other elements known to the art. A first portion of the collected light is directed into device 7 (a detector) which measures the intensity spectrum $|H(\omega)|$ of the transmitted light. Device 7 can be an optical spectrum analyzer, monochromator, spectrograph, FTIR or any other type of device that measures the spectrum of the light with suitable sensitivity and spectral resolution over a suitable spectral range that is at least equal to SW.

A second portion of the light transmitted through 4 is directed by element 6 onto device 8. Element 6 is a beam divider, which can be a dichroic beam splitter, fiber coupler, or any other device that can divert a portion of the light collected by optics 5 in another direction from the portion that is transmitted to device 7. Device 8 splits the second portion of light into N spectral components, from $\omega_1$ to $\omega_N$, and diverts those components onto device 9, which in one embodiment is a set of detectors emitting electronic signals D1, D2 ... DN in response to the N spectral components that is received. In a preferred embodiment, 8 is an optical grating, but can be any optical device that divides the light into the desired spectral components.

Each of the signals D1 to DN is proportional to $\cos(\Omega t+\Delta\theta(\omega_j))$, where j=1, 2, ... N. $\Delta\theta(\omega_j)$ is the phase lag of signal Dj relative to that of the signal $\cos(\Omega t)$ of signal generator 20, and as explained above, after division by $\Omega$ is approximately the derivative of the optical phase acquired by spectral component $\omega_j$ due to the medium 4. The value of $\Delta\theta(\omega_j)$ for the N signals 10 is measured electronically by directing the N signals 10 into component 11 together with the modulation signal 22 from signal generator 20. In one embodiment 11 is an RF phase detector where each of the N outputs are the N phase lags of the N signals D1 ... DN relative to the input signal from 20. In another embodiment, 11 is a set of N electronic phase detectors, each of which determines one of the N phase lags. In some embodiments, 20 is another type of electronic device known in the art that is capable of determining the phase difference between at least two RF signals.

The values of the N phase lags are inputted to computer 14 via electronic path 13. Computer 14 also receives as input the intensity spectrum $|H(\omega)|^2$, from 7 via electronic path 12 and computes ln $|H(\omega)|$ for each of the measured spectral components, as disclosed in the discussion hereinabove. Computer 14 now has all of the necessary information necessary to carry out a calculation of the phase spectrum or its' derivative. This is done either through the use of the KK algorithm, which as disclosed above uses equation (16) to compute $\Delta\theta(\omega)$ and then perform a summation as described in equation (19) to determine the phase spectrum $\theta(\omega)$, or as disclosed above for the MEM-based algorithm, which uses eq. (25) to compute the error-phase derivative at the anchoring points, and the procedure disclosed after eq. (25) to determine the phase spectrum itself; or, as disclosed in the DKK method, to calculate an improved phase spectrum as described in eq. (29).

In the system depicted in FIG. 6, transmitted light is collected for analysis. In some embodiments, light reflected from medium 4 is collected for analysis as described for the case of absorption.

Additional Details Relating to DKK, as Well as DMSKK and MEM with SPEBI

According to an additional aspect of the invention, there is provided a method for determining an (in some embodiments electromagnetic) phase spectrum $\theta(\omega)$ of the complex spectral transfer function $H(\omega)$ of a volume of an object, where $\ln[H(\omega)] = \ln(|H(\omega)|) + i\theta(\omega)$, the method comprising:

a. acquiring an (in some embodiments electromagnetic) amplitude spectrum $|H(\omega)|$ of a complex spectral transfer function $H(\omega)$ of a volume of an object;

b. determining an nth derivative of the phase spectrum $d^n\theta(\omega)/d\omega^n$ of the complex spectral transfer function $H(\omega)$, from the acquired amplitude spectrum $|H(\omega)|$; and c. integrating the $d^n\theta(\omega)/d\omega^n$ times to acquire an phase spectrum $\theta(\omega)$ of the complex spectral transfer function, wherein n is an integer of at least 0. In some embodiments, n is 0 and the object scatters the wavelengths of radiation making up $|H(\omega)|$. In some embodiments, n is 1 and the nth derivative is a first derivative. In some embodiments, n is 2, and the nth derivative is a second derivative. In some embodiments, n is 3, and the nth derivative is a third derivative.

In some embodiments, the nth derivative of the phase spectrum $d^n\theta(\omega)/d\omega^n$ is determined by:

calculating an nth derivative $d^n|H(\omega)|/d\omega^n$ of the acquired amplitude spectrum $|H(\omega)|$; and applying a phase-retrieval procedure on the $d^n|H(\omega)|/d\omega^n$, thereby determining the $d^n\theta(\omega)/d\omega^n$.

In some embodiments, the nth derivative of the phase spectrum $d^n\theta(\omega)/d\omega^n$ is determined by:

calculating an nth derivative $d^n \ln(|H(\omega)|)/d\omega^n$ of the acquired amplitude spectrum $|H(\omega)|$; and applying a phase-retrieval procedure on the $d^n \ln(H(\omega))/d\omega^n$, thereby determining the $d^n\theta(\omega)/d\omega^n$. In some embodiments, the phase-retrieval procedure is the Kramers-Kronig (KK) relation. In some embodiments, the phase-retrieval procedure is the maximum entropy method (MEM) technique.

According to an aspect of some embodiments of the invention, there is also provided a method for detecting (in some embodiments, even imaging) an object screened by a volume of a scattering medium, comprising:

a) providing a transmitter;

b) projecting a beam of radiation (in some embodiments, electromagnetic radiation) from the transmitter to interact with a volume of a scattering medium, the beam comprising a plurality of wavelengths of radiation;

c) using a detector to acquire an amplitude spectrum $|H(\omega)|$ of a complex spectral transfer function $H(\omega)$, where $\ln[H(\omega)] = \ln(|H(\omega)|) + i\theta(\omega)$, of the volume of the scattering medium;

d) determining an phase spectrum $\theta(\omega)$ of the complex spectral transfer function $H(\omega)$ of the volume of the scattering medium, for example as described herein; and d) determining an phase spectrum $\theta(\omega)$ of the complex spectral transfer function $H(\omega)$ of the volume;

e) calculating the complex spectral transfer function $H(\omega)$ of the volume from the acquired amplitude spectrum $|H(\omega)|$ and the determined phase spectrum $\theta(\omega)$; and f) converting the calculated $H(\omega)$ to the impulse response $h(t)$ of the volume.

In some embodiments, once $h(t)$ is determined (including using the DMSKK, MEM with SPEBI or DKK embodiments), the presence or absence of an object screened by the volume of the scattering medium is determined. Generally, detecting the presence or absence of the object is performed in the usual way from $h(t)$, for example by using the "first light" method discussed in the introduction, or as detailed hereinbelow.

In some embodiments, the detector is positioned to acquire the $|H(\omega)|$ from radiation passing through the volume of scattering medium (e.g., transmission imaging). In some such embodiments, the volume of medium is disposed between the transmitter and the detector.

In some embodiments, the detector is positioned to acquire the $|H(\omega)|$ from radiation reflected from the volume of scattering medium (e.g., reflection imaging). In some such embodiments, the transmitter and the detector are found on the same side of the volume of medium.

In some embodiments, the scattering medium is biological tissue. In some such embodiments, the object to be detected is selected from the group consisting of abnormalities, cancerous growth and sub-surface tissue structures. In some such embodiments, the beam comprises electromagnetic radiation having visible and/or near-infrared wavelengths.

In some embodiments, the medium is an optical element or a semiconductor material, such as a lens, a wave guide or a wafer. In some such embodiments, the object to be detected is a defect in the optical element or the semiconductor material. In some such embodiments, the beam comprises electromagnetic radiation having ultraviolet, visible, infrared and/or far-infrared wavelengths.

In some embodiments, the medium is an atmospheric scattering medium such as water-vapor, fog, mist, clouds, smoke, rain, haze, steam or dust. In some such embodiments, the object to be detected is a man-made object, such a ground vehicle or an airplane. In some such embodiments, the beam comprises electromagnetic radiation having radio and/or microwave wavelengths. In some such embodiments, the transmitter and the detector comprise elements of a radar installation. In some such embodiments, the beam comprises electromagnetic radiation having ultraviolet, visible, infrared and/or far-infrared wavelengths.

In some embodiments, the medium comprises fiber, such as clothing or cloth. In some such embodiments, the object to be detected is a man-made object hidden by the clothing. In some such embodiments, the beam comprises electromagnetic radiation having visible and/or near-infrared wavelengths. In some such embodiments, the beam consists essentially of eye-safe wavelengths. In some such embodiments, the beam comprises electromagnetic radiation having wavelengths of between 0.5 and 3 micrometers.

According to an aspect of some embodiments of the invention, there is also provided a method for determining a refractive index spectrum of a volume of an object, comprising:
  a) providing a transmitter;
  b) projecting a beam of radiation (in some embodiments, electromagnetic radiation) from the transmitter to interact with a volume of an object;
  c) using a detector to acquire an (in some embodiments electromagnetic) amplitude spectrum $|H(\omega)|$ of a complex spectral transfer function $H(\omega)$ of the volume of the object, where $\ln [H(\omega)] = \ln(|H(\omega)|) + i\, \theta(\omega)$;
  d) determining an phase spectrum $\theta(\omega)$ of the complex spectral transfer function $H(\omega)$ as described herein; and
  e) calculating the complex spectral transfer function $H(\omega)$ of the volume of the object from the acquired amplitude spectrum $|H(\omega)|$ and the determined phase spectrum $\theta(\omega)$
thereby determining a refractive index spectrum which is the complex spectral transfer function $H(\omega)$ of the volume of the object.

In some embodiments, the detector is positioned to acquire the $|H(\omega)|$ from radiation passing through the volume of the object. In some such embodiments, the volume of the object is disposed between the transmitter and the detector.

In some embodiments, the detector is positioned to acquire the $|H(\omega)|$ from radiation reflected from the volume of the object. In some such embodiments, the transmitter and the detector are found on the same side of the volume of the object.

According to an aspect of some embodiments of the invention, there is also provided a device suitable for determining an (in some embodiments electromagnetic) phase spectrum $\theta(\omega)$ of the complex spectral transfer function $H(\omega)$ of a volume of an object, comprising:
  a) a transmitter, configured to project a beam of radiation (in some embodiments, electromagnetic radiation) at a volume of an object of interest;
  b) a detector configured to acquire the radiation projected by the transmitter subsequent to interaction with the volume and to output an amplitude spectrum $|H(\omega)|$ of the acquired radiation; and
  c) a signal analysis assembly functionally associated with the detector, configured to:
    obtain the amplitude spectrum $|H(\omega)|$ from the detector; and calculate an phase spectrum $\theta(\omega)$ of the complex spectral transfer function $H(\omega)$, where $\ln [H(\omega)] = \ln(|H(\omega)|) + i\theta(\omega)$ of the volume as described herein from the amplitude spectrum $|H(\omega)|$.

In some embodiments, the signal analysis assembly is configured to automatically perform the calculation.

In some embodiments, a device suitable for implementing an embodiment (e.g., DKK, DMSKK, MEM with SPEBI) is configured to project the beam at an object that substantially comprises a scattering medium such as biological tissue. In some such embodiments, the beam comprises electromagnetic radiation having visible and/or near-infrared wavelengths.

In some embodiments, a device suitable for implementing an embodiment (e.g., DKK, DMSKK, MEM with SPEBI) is configured to project the beam at an object that substantially comprises a scattering medium such as an optical element or a semiconductor material. In some embodiments, the beam comprises electromagnetic radiation having ultraviolet, visible, infrared and/or far-infrared wavelengths.

In some embodiments, a device suitable for implementing an embodiment (e.g., DKK, DMSKK, MEM with SPEBI) is configured to project the beam at an object that substantially comprises an atmospheric scattering medium such as water-vapor, fog, mist, clouds, smoke, rain, haze, steam or dust. In some such embodiments, the beam comprises electromagnetic radiation having radio and/or microwave wavelengths. In some such embodiments, the transmitter and the detector comprise elements of a radar installation. In some such embodiments, the beam comprises electromagnetic radiation having ultraviolet, visible, infrared and/or far-infrared wavelengths.

In some embodiments, a device suitable for implementing an embodiment of the invention (e.g., DKK, DMSKK, MEM with SPEBI) is configured to project the beam at an object that substantially comprises a scattering medium such as fibers, such as clothing. In some such embodiments, the beam comprises electromagnetic radiation having visible and/or near-infrared wavelengths. In some such embodiments, the beam consists essentially of radiation having eye-safe wavelengths. In some embodiments, the beam comprises radiation having wavelengths of between 0.5 and 3 micrometers.

In some embodiments, a device suitable for implementing an embodiment of the invention (e.g., DKK, DMSKK, MEM with SPEBI) is configured to determine a refractive index spectrum of the volume of the object. In some such embodiments, the device is configured to report a refractive index spectrum of the volume of the object.

In some embodiments, the detector of a device suitable for implementing an embodiment of the invention (e.g., DKK, DMSKK, MEM with SPEBI) is positioned to acquire the $|H(\omega)|$ from radiation passing through a volume of an object of interest. In some such embodiments, the transmitter and the detector are positioned to allow the object of interest to be positioned therebetween, for example allowing transmission imaging.

In some embodiments, the detector of a device suitable for implementing an embodiment of the invention (e.g., DKK, DMSKK, MEM with SPEBI) is positioned to acquire the $|H(\omega)|$ from radiation reflected from a volume of an object of interest. In some such embodiments, the detector is configured to acquire the radiation from the same side of the object of interest where the transmitter is located, for example allowing reflection imaging.

Detector

In some embodiments, a detector for implementing a method or device of the invention is an assembly configured to determine the intensity of radiation as a function of wavelength of the desired range of wavelengths, that is to say, the detector is configured to acquire a spectrum having a spectral width of at least the desired range of wavelengths.

The desired range of wavelengths is such that the achieved resolution is sufficient. As is known to one skilled in the art, to achieve a desired physical resolution of $\Delta x$ a sufficient spectral width $\Delta f$ is required, where $\Delta x = c/\Delta f$.

In some embodiments, a detector is configured to determine the intensity of no more than the desired range of wavelengths. In some embodiments, the detector is configured to determine the intensity of a range of wavelengths broader than the desired range.

A detector is implemented using any suitable technology. In some embodiments, the detector comprises a spectrometer, an optical spectrum analyzer, a monochromator, a spectrograph or an FTIR device. In some embodiments, the detector comprises a component selected from the group consisting of a lens, an antenna, a photon detector and a charge-coupled device (CCD). In some embodiments, the intensity of radiation of a limited number of wavelengths (in embodiments a single wavelength) is determined at any one time and the desired range of wavelengths is scanned. In some embodiments, the intensity of radiation of substantially all the wavelengths of the desired range of wavelengths is determined substantially at the same time.

Transmitter

In some embodiments, a transmitter for implementing a method or a device of the invention is configured to project a beam comprising a plurality of wavelengths of radiation, in some embodiments, electromagnetic radiation. In some embodiments, a transmitter projects a continuous wave (cw) beam of radiation. In some embodiments, a transmitter projects a broad band beam of radiation.

When implementing some aspects of the invention, it is important that the beam of radiation comprising a plurality of wavelengths projected by the transmitter and interacting with the volume has a sufficient spectral width, that is to say, includes at least the desired range of wavelengths.

In some embodiments, the intensity of the plurality of wavelengths in the desired range of wavelengths constituting the beam is uniform. That said, in some embodiments, the intensity of the plurality of wavelengths in the desired range of wavelengths constituting the beam is not uniform, for example has a Gaussian or other distribution.

Suitable transmitters include laser, light-emitting diodes, ultrasonic transducers and other sources of radiation. A suitable transmitter for implementing some embodiments of the invention is a broadband laser. Some suitable broadband lasers are tunable and configured to project electromagnetic radiation of between about 700 nm and about 1000 nm, for example a Model 890 Titanium: Sapphire Laser by Coherent, Inc. Santa Clara, Calif., USA.

In some embodiments, the beam of radiation comprises a plurality of wavelengths selected to have a relatively high transmission through the medium, especially in embodiments where the transmitter and the detector are positioned to allow the medium to be positioned therebetween.

Detailed Development of DKK Embodiment

As stated above, in real experiments only a finite spectrum is measured, and as a consequence the phase can only be calculated approximately by applying the Kramers-Kronig relation to the function:

$$f_1(\omega) = \begin{cases} \ln|H(\omega)| & \omega_L \leq \omega \leq \omega_H \\ 0 & \text{else} \end{cases} \quad (30)$$

That is $$\theta_{KK}(\omega) = -\frac{1}{\pi} P \int_{\omega_L}^{\omega_H} d\omega' \frac{\ln|H(\omega')|}{\omega' - \omega} \quad (31)$$

Since the phase does not have an absolute physical meaning but only a relative one, it may be more instructive to calculate the spectral derivative of the phase, i.e., the time delay $$\tau_{KK}(\omega) \equiv \frac{d\theta_{KK}(\omega)}{d\omega} = -\frac{1}{\pi} \frac{d}{d\omega} P \int_{\omega_L}^{\omega_H} d\omega' \frac{\ln|H(\omega')|}{\omega' - \omega} \quad (32)$$

The effects of the finite boundaries were discussed extensively in the literature, and various techniques have been developed to deal with this issue [Refs. 8, 12, 13 and 22].

Surprisingly, it has been found that the Kramers-Kronig relation can be applied to the spectral derivative of $H(\omega)$, that is to say that if the Kramers-Kronig relation can be applied to $\ln H(\omega)$ (which means that $\ln H(\omega)$ is the transfer function of a causal system), then the relation can also be applied to $d \ln H(\omega)/d\omega$ (which would also correspond to a causal system). Since (see above)

$$\frac{d\ln[H(\omega)]}{d\omega} = \frac{d\ln|H(\omega)|}{d\omega} + i\frac{d\theta}{d\omega} \quad (13)$$

the Kramers-Kronig relation for the time-delay can be written $$\tau_{DKK}(\omega) = -\frac{1}{\pi} P \int_{\omega_L}^{\omega_H} d\omega' \frac{1}{\omega' - \omega} \frac{d}{d\omega'} \ln|H(\omega')|. \quad (33)$$

where Eqs. (32) and (33) express the same time delay differently.

The possibility of working with the spectral derivatives of the intensity and phase has been demonstrated in spectral techniques of the Inventors [Refs. 10, 14, 15], which favor measurements of the phase derivatives rather than the phase itself. Phase derivatives are simpler to measure and are related to an unambiguous physical realization (i.e. time delay).

Since in Eq. (32) one can swap the derivative with the integral, the equation is rewritten:

$$\tau_{KK}(\omega) = -\frac{1}{\pi} P \int_{\omega_L}^{\omega_H} d\omega' \ln|H(\omega')| \frac{d}{d\omega}\left(\frac{1}{\omega' - \omega}\right) \quad (34)$$

$$= \frac{1}{\pi} P \int_{\omega_L}^{\omega_H} d\omega' \ln|H(\omega')| \frac{d}{d\omega'}\left(\frac{1}{\omega' - \omega}\right)$$

and therefore the difference between Eq. (32) (or Eq. 34) and (Eq. 33) is $$\tau_{DKK}(\omega) - \tau_{KK}(\omega) = -\frac{1}{\pi} P \int_{\omega_L}^{\omega_H} d\omega' \frac{d}{d\omega'}\left(\frac{\ln|H(\omega')|}{\omega' - \omega}\right) \quad (35)$$

$$= -\frac{1}{\pi}\left(\frac{\ln|H(\omega_H)|}{\omega_H - \omega} - \frac{\ln|H(\omega_L)|}{\omega_L - \omega}\right)$$

This suggests that for any causal medium $|H(\Omega)| \to 1$ for $\Omega \to \pm\infty$, since if the spectral domain is infinite (i.e., $\omega_L \to -\infty$ and $\omega_H \to +\infty$) the difference Eq. (35) must vanish for the causality condition to be upheld, i.e., Eqs. (33) and (34) converge to the same expression. It should be stressed that Eq. (35) should be arbitrarily small even if the spectral width is arbitrarily large—but finite. Only $|H(\omega)| \to 1$ will keep this requirement. However, for any spectrum with finite bandwidth the two expressions are considerably different. The question of which one is better depends of course on the true values of $|H(\omega)|$ beyond the bounded spectral domain (i.e. at $\omega > \omega_H$ and $\omega < \omega_L$).

However, there is an important distinction between the two: Eq. (32) diverges as $\omega^{-1}$ at the boundaries of the spectrum, while in Eq. 33 the divergence is considerably weaker, at worst diverging logarithmically. Moreover, one way to artificially eliminate the divergence at the boundaries of Eq. (32) is to apply the Kramers-Kronig relation to the function:

$$f_2(\omega) = \begin{cases} \ln|H(\omega_L)| & \omega < \omega_L \\ \ln|H(\omega)| & \omega_L \leq \omega \leq \omega_H \\ \ln|H(\omega_H)| & \omega > \omega_H \end{cases} \quad (36)$$

instead of $f_1(\omega)$ That is, it is assumed that there is no change in the spectrum's amplitude beyond the measured range $\omega_L \leq \omega \leq \omega_H$. For this case the delay time is $$\tau_2 = \tau_{KK} + \frac{\ln|H(\omega_L)|}{\pi}\frac{1}{\omega_L - \omega} - \frac{\ln|H(\omega_H)|}{\pi}\frac{1}{\omega_H - \omega}. \quad (37)$$

It is noted that this is exactly $\tau_{DKK}$.

It is therefore apparent that for a finite bandwidth spectrum, application of the Kramers-Kronig relation to the spectral derivative of $H(\omega)$, has a higher chance of yielding better results than application of the Kramers-Kronig relation to $H(\omega)$. Application of the Kramers-Kronig relation to $d \ln H(\omega)/d\omega$ effectively assumes a continuation at the boundaries points, while application to $\ln H(\omega)$ assumes an abrupt change (zero values beyond the known spectral domain).

Therefore, the Kramers-Kronig relation for a finite spectrum Eq. (31) can be improved by integrating Eq. (33):

$$\theta_{DKK}(\omega) - \theta(\omega_0) = \int_{\omega_0}^{\omega} d\omega' \tau_{dKK}(\omega') \quad (38)$$
$$= \frac{1}{\pi} P \int_{\omega_L}^{\omega_H} d\omega' \ln\left(\frac{\omega - \omega'}{\omega_0 - \omega'}\right) \frac{d}{d\omega'} \ln|H(\omega')|$$

For most practical purposes one can take $\omega_0 = 0$ and therefore $\theta(\omega_0) = 0$, yielding $$\theta_{DKK}(\omega) = \frac{1}{\pi} P \int_{\omega_L}^{\omega_H} d\omega' \ln\left(1 - \frac{\omega}{\omega'}\right) \frac{d}{d\omega'} \ln|H(\omega')| \quad (39)$$

Higher-Order Derivatives

The relations described for the first derivative $d \ln H(\omega)/d\omega$ can be generalized to higher-order derivatives. In particular, the Hilbert transform can be operated on the nth derivative of the TF:

$$\frac{d^n \ln[H(\omega)]}{d\omega^n} = \frac{d^n \ln|H(\omega)|}{d\omega^n} + i\frac{d^n\theta}{d\omega^n} \quad (40)$$

which yields the more general relation:

$$\frac{d^n\theta}{d\omega^n} = -\frac{1}{\pi} P \int_{\omega_L}^{\omega_H} d\omega' \frac{1}{\omega' - \omega} \frac{d^n}{d\omega'^n} \ln|H(\omega')| \quad (41)$$

One can combine the two derivative techniques, for example to calculate $$\frac{d^n\theta}{d\omega^n}$$

one takes the qth derivative of Eq. (2), and applies the Hilbert transform on:

$$\frac{d^q \ln[H(\omega)]}{d\omega^q} = \frac{d^q \ln|H(\omega)|}{d\omega^q} + i\frac{d^q\theta}{d\omega^q} \quad (42)$$

Yielding:

$$\frac{d^q\theta}{d\omega^q} = -\frac{1}{\pi} P \int_{\omega_L}^{\omega_H} d\omega' \frac{1}{\omega' - \omega} \frac{d^q}{d\omega'^q} \ln|H(\omega')| \quad (43)$$

Then, the (n−q)th derivative of this result gives $$\frac{d^n\theta}{d\omega^n} = \frac{1}{\pi} P \int_{\omega_L}^{\omega_H} d\omega' \frac{d^{n-q}}{d\omega^{n-q}} \left[\frac{1}{\omega - \omega'}\right] \frac{d^q}{d\omega'^q} \ln|H(\omega')| \quad (44)$$
$$= -\frac{(n-q)!}{\pi} P \int_{\omega_L}^{\omega_H} d\omega' (\omega' - \omega)^{-(n-q+1)} \frac{d^q}{d\omega'^q} \ln|H(\omega')|$$

The regular Kramers-Kronig case is restored for $q=0$, while Eq. 41 is obtained by taking $q=n$.

To restore the phases (instead of their derivatives) a series of integrals over Eq. 41 yields (for $n \geq 2$)

$$\theta(\omega) - \Theta_{n-1}(\omega) = \quad (45)$$
$$\frac{1}{\pi} P \int_{\omega_L}^{\omega_H} d\omega' \left\{\frac{(\omega - \omega')^{n-1}}{(n-1)!}\left[\ln(\omega - \omega') - \frac{\omega'(n-1)}{\omega - \omega'} - \sum_{m=1}^{n-1}\frac{1}{m}\right]\right\} \frac{d^n}{d\omega'^n} \ln|H(\omega')|$$

where $\Theta_{n-1}(\omega)$ is a polynomial of degree $n-1$.

Using techniques described in the art [e.g., Ref. 4], the two above-discussed methods were compared by simulating a medium with 1000 delta function scatterers. Each one of these scatterers simulates, with high accuracy, a narrow glass plate whose width is distributed uniformly between 0 and 30 nm. Similarly, the distance between two adjacent scatterers is distributed uniformly between 0 and 5 μm. The TF of such a medium was calculated (both amplitude and phase) in the finite spectral range 300.6 THz$\leq f \leq$301.2 THz. Then the amplitude calculations were substituted into Eqs. 32 and 33 to evaluate the time delay in the two methods.

Figure 7:
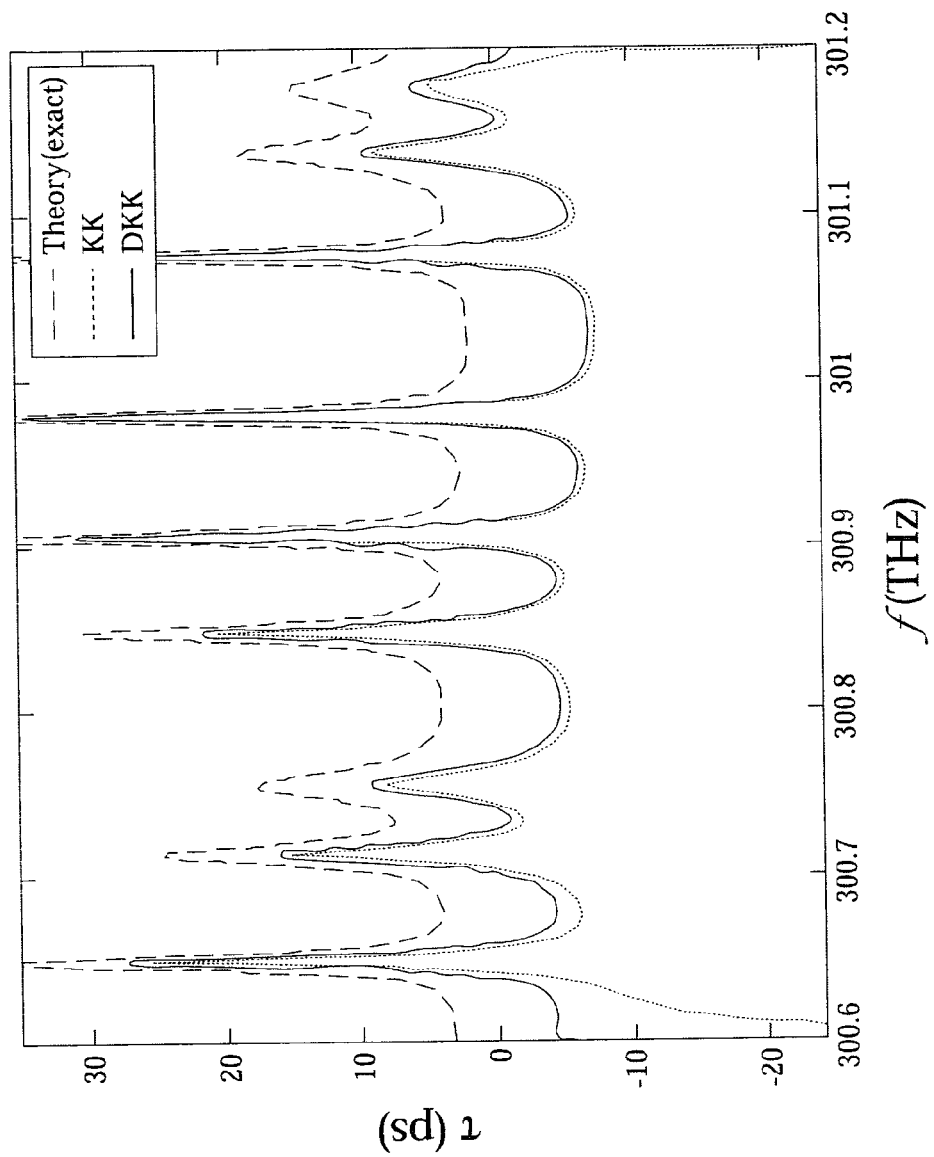
FIG. 7 depicts the results of a simulation of a spectrum of a scattering medium comparing the exact analytic solution (dotted line), the known Kramers-Kronig method (KK, Eq. 32) and an embodiment of the invention (DKK, Eq. 33)

In FIG. 7, theoretical exact analytic spectrum (dashed line) is compared to the results found applying the Kramers-Kronig relation to $\ln H(\omega)$ ($\tau_{KK}$ Eq. 32, dotted line) and applying the Kramers-Kronig relation to the first derivative $d \ln H(\omega)/d\omega$ ($\tau_{DKK}$, Eq. 33, solid line). Both methods result in a spectrum that is slightly shifted in value from theoretical one since they evaluate the phase difference (or the time delay) only up to a constant value.

As is seen from FIG. 7, application to the derivative in accordance with the invention yields superior results, especially at the boundaries, but also inside the spectral region. The divergence at the boundaries is much milder for the DKK method than for the KK method: the divergence is logarithmic, barely noticeable at the edge of the lower boundary.

Figure 8:
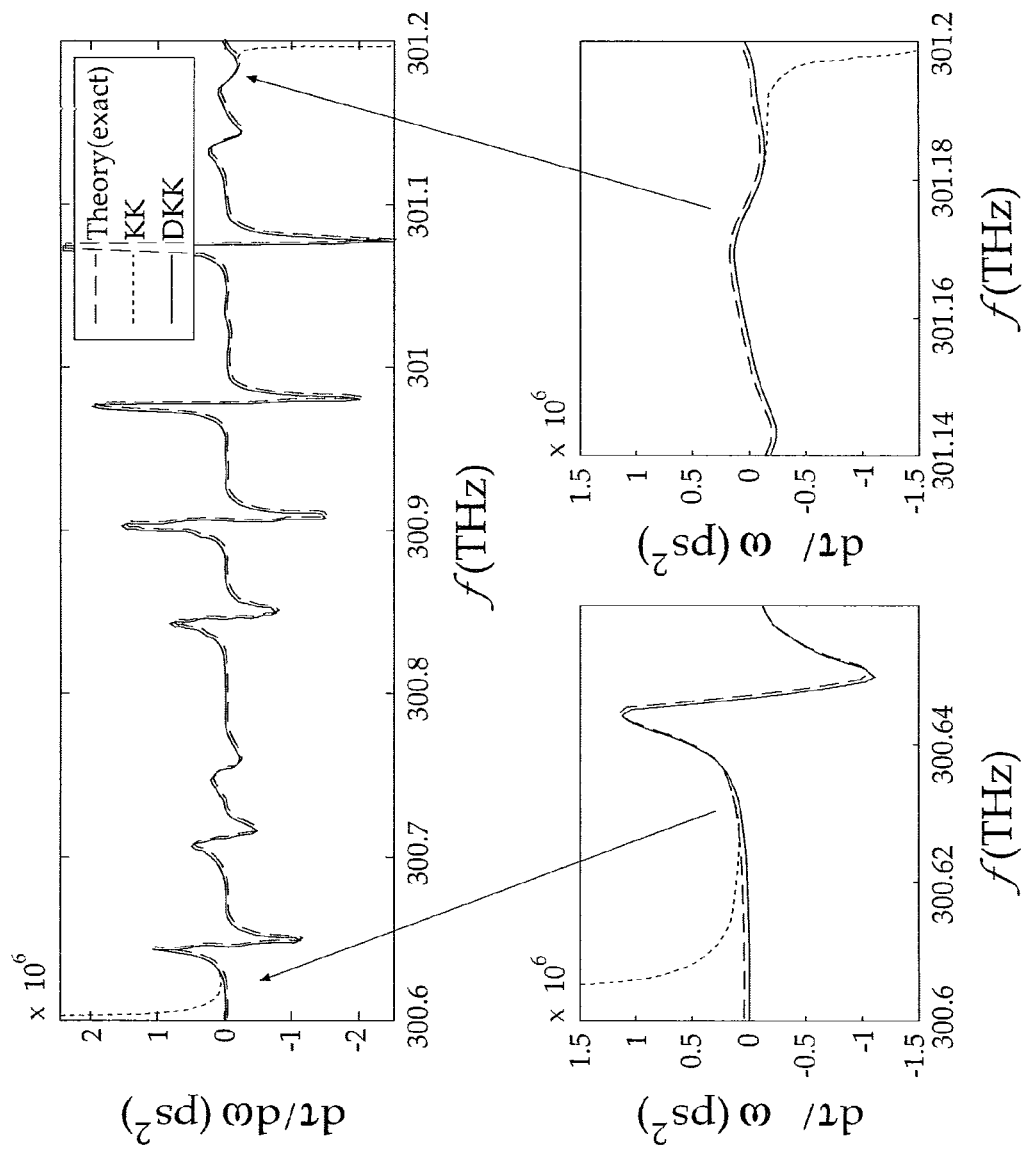
FIG. 8 depicts the results of $d\tau/d\omega = d^2\theta/d\omega^2$ of a simulation of a scattering medium, comparing the exact analytic solution (dashed line), the known Kramers-Kronig method (KK, Eq. 45) and an embodiment of the invention (DKK, Eq. 46)

In FIG. 8 the comparison between the two methods is presented for the second spectral derivative (or the spectral derivative of the time delay). The dotted line shows the second derivative, calculated using the know Kramers-Kronig (KK) technique, i.e., $$\frac{d\tau_{KK}}{d\omega} \equiv \frac{d^2\theta_{KK}(\omega)}{d\omega^2} = -\frac{1}{\pi}\frac{d^2}{d\omega^2}P\int_{\omega_L}^{\omega_H}d\omega'\frac{\ln|H(\omega')|}{\omega'-\omega} \quad (46)$$

while the solid line displays the second derivative which was derived in accordance with an embodiment of the invention (DKK), i.e., $$\frac{d^2\theta}{d\omega^2} = -\frac{1}{\pi}P\int_{\omega_L}^{\omega_H}d\omega'\frac{1}{\omega'-\omega}\frac{d^2}{d\omega'^2}\ln|H(\omega')| \quad (47)$$

In FIG. 8, there is seemingly no divergence from the exact theoretical result seemingly disappears when the DKK method is used to calculate the second derivative $d^2\theta/d\omega^2 = d\tau/d\omega$, whereas in practice the divergence becomes milder (logarithmic) but does not disappear completely (see Eq. 45). On the other hand, as pointed out above, the ordinary Kramers-Kronig technique forms singularities at the boundaries of the spectral range (see detailed graphs in FIG. 8). Moreover, the constant shift between theoretical result (the solid line) and the derived ones, which appears for the time-delay analysis (FIG. 7), disappears in this case since the mean value of the second derivative is zero, and the results are much more accurate.

It should be stressed that the improvement was not achieved by using additional data (as taught in Ref. 23) or by extrapolating the known measured data outside the spectral range (as taught in Ref. 4). Rather, the improvement was achieved in accordance with an embodiment of the teachings of the invention: instead of applying the Kramers-Kronig relations to calculate the phase and only then to take its derivatives, the spectral derivatives are taken prior to the Hilbert transform operation. This operation is equivalent to applying the Hilbert transform (and its derivative) on an extrapolation of the original function beyond the spectral domain (e.g., Eq. 36).

Clearly, if this method is applied to determine the phase of a spectrum (instead of its derivatives) then information is lost. For example in such a case for n=2 Eq. 44 becomes:

$$\theta(\omega) - c_1\omega - c_0 = \quad (48)$$
$$\frac{1}{\pi}P\int_{\omega_L}^{\omega_H}d\omega'\{(\omega-\omega')\ln[(\omega-\omega')/e] - \omega'\}\frac{d^2}{d\omega'^2}\ln|H(\omega')|$$

where there is no trace of the singularities of the original Eq. 31, i.e., there are no terms which diverge for $\omega' \to \omega$ (provided of course, that the TF is a smooth analytical function). On the other hand, this procedure gives at most two additional unknowns $c_0$ and $c_1$.

The values of the unknowns can be evaluated by one or two phase measurements (in practice, since the phase has only a relative meaning $-c_0$ is usually redundant). This can explain the strength of the technique, for example as embodied in Eq. 40: the finite spectral range analysis is partially compensated by anchoring the phase at specific frequencies (i.e., a few phase measurements can help to evaluate the entire spectrum, for example measured using the SPEBI technique (Refs. 10, 14-16). In such embodiments, the same analysis is done on the phase difference. The original motivation was that phase differences are easier to measure. However, from the analysis herein it is surmised that the main strength lies in the fact that it operates on the derivatives of the TF instead of the TF directly. As a consequence, the divergences at the spectral boundaries are reduced substantially and there is a need for at most two measured quantities to reproduce the original spectrum with great accuracy.

Thus, the utility of the application of the Kramers-Kronig relation on the nth-order spectral derivatives of a TF in accordance with embodiments of the teachings of the invention has been demonstrated. The results of this operation are expressions for the nth-order spectral derivatives of the phase spectrum. For a finite spectral range this yields results superior to prior applications of the Kramers-Kronig relations. When prior Kramers-Kronig relations are applied on a finite range spectrum, divergences appear near the spectrum's boundaries. These divergences become considerably milder and, for all practical purposes, disappear when the teachings of the invention are applied to data with the second derivative. Thus, the teachings of the invention improve the phase derivatives evaluations not only at the boundaries but at the center of spectral domain as well.

Working with the derivatives of the TF instead of the TF itself, leads to (n−1) unknown parameters when restoring the phase spectrum. In some embodiments, this is alleviated by anchoring the phase-derivative spectrum with the use of a limited number of actually-measured phase values, e.g., for example measured using the SPEBI technique (Refs. 10, 14-16). In some embodiments, the phase-derivative spectrum, i.e., the time-delay dependence on frequency is the desired result. Some embodiments of the invention are optionally used together with the methods described in Ref. 23. In some such embodiments, the Kramers-Kronig relation is applied on an nth derivative of the logarithm of the amplitude so that the nth derivative of the phase (instead of the phase itself) may be evaluated and anchored. This is a very important distinction due to the fact that phase derivatives are much easier to actually measure. Therefore, it is seen that application of the Kramers-Kronig relation on the nth derivative provides an advantage over an ordinary Kramers-Kronig relation, including 1) the singularities at the spectral boundaries become milder and 2) the results can be integrated with phase derivatives measurements, which are much easier to perform than phase measurements.

In some embodiments, the nth derivates described herein are optionally applied together with the maximum entropy method (MEM) technique. One of the benefits is that the phase derivative may be measured relative easily. In some embodiments, the higher derivatives are applied together with the MEM technique: The phase that the MEM technique calculates is evaluated and then an nth (n an integer at least 1) derivative of the calculated phase is taken and the error of the derivative is calculated, then multiplied by a Lagrange polynomial, which fixes the phase nth derivative at specific frequencies (i.e., phase derivatives anchoring) and return to phases by simple integration (or multiple integrations).

Device and Method for Determining a Refractive Index Spectrum of a Material

The complex spectral transfer function $H(\omega)$ of a material is a refractive index spectrum of that material and is considered to be a detailed description of the spectral properties of a material, especially as relates to impulse response and interaction with radiation. As such, determination of a refractive index spectrum of a material is of the utmost importance in many fields such as optics, semiconductors and material science, both for evaluating the utility of novel materials and for providing definitive quality control of manufactured components such as optical fibers, semiconductor wafers and the like.

In some embodiments, aspects of the invention are applied to determine a refractive index spectrum of a material. An embodiment including DKK to determine the refractive index spectrum of a material is described in detail hereinbelow. A person having ordinary skill in the art is, upon perusal of the description herein, able to make the appropriate modifications to apply other embodiments of the invention including DMSKK and MEM with SPEBI.

Figure 9A:
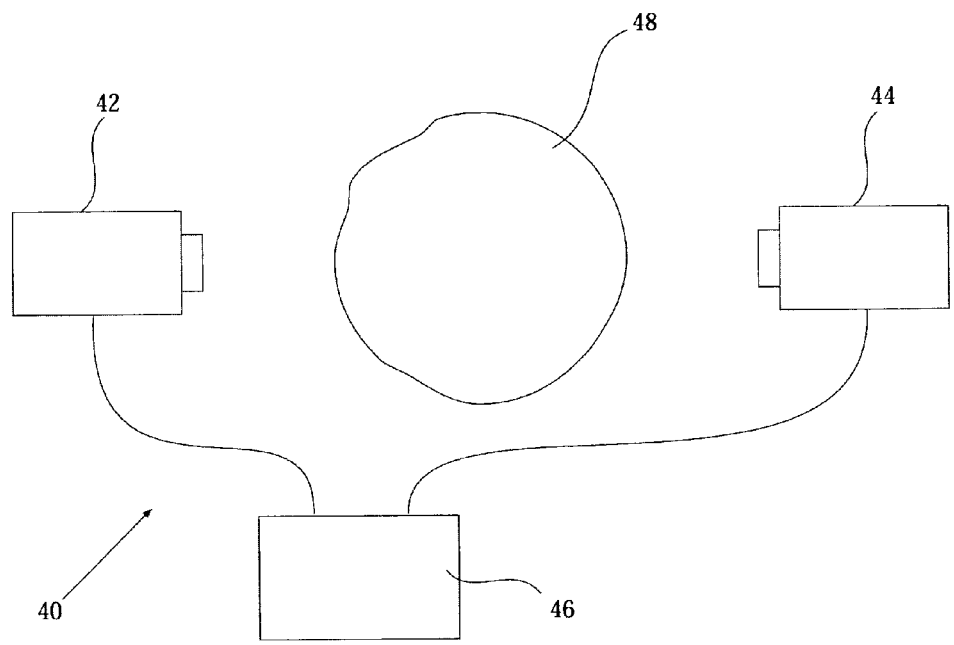
FIGS. 9A and 9B are schematic depictions of devices useful for implementing aspects of the present invention.

In FIG. 9A, a device 40 for determining a refractive index spectrum of a material is depicted, comprising a transmitter 42 (a broadband laser), a detector 44 (a spectrometer) and a signal analysis assembly 46 (an appropriately configured general purpose computer) functionally associated with detector 44.

An object of interest 48 is placed between transmitter 42 and detector 44.

Transmitter 42 is activated to project a beam of radiation (e.g., electromagnetic radiation, including ultraviolet light, visible light, infrared light (near and far) or a combination) through object of interest 48. The beam interacts with the volume of material of object 48 through which the beam passes.

Detector 14, in the usual way, acquires the intensity as a function of frequency $\omega_i$ of radiation projected by transmitter 42 subsequent to interaction with the volume of material of object 48.

For each frequency $\omega_i$, projected by transmitter 42 with an intensity $I_{transmitter}(\omega_i)$ and detected by detector 44 with an intensity $I_{detector}(\omega_i)$, $|H(\omega_i)|^2 = I_{detector}(\omega_i)/I_{transmitter}(\omega_i)$. Thus, the amplitude spectrum $|H(\omega)|$ of the complex spectral transfer function $H(\omega)$ of the volume of material is acquired, where $\ln[H(\omega)] = \ln(|H(\omega)|) + i\theta(\omega)$. Detector 44 outputs the acquired amplitude spectrum $|H(\omega)|$ (e.g., a computer-readable representation of the spectrum) to signal analysis assembly 46, in the usual way.

Signal analysis assembly 46 (e.g., a general purpose computer running Mathematica 7, Wolfram Research Inc, Champaign, Ill., USA) determines an phase spectrum $\theta(\omega)$ of the complex spectral transfer function $H(\omega)$ as described above in accordance with the invention.

Specifically, an nth derivative (in some embodiments n=0, n=1, n=2, n=3 or even greater) of the phase spectrum $d^n\theta(\omega)/d\omega^n$ is determined from the acquired amplitude spectrum $|H(\omega)|$. As noted above, in some embodiments, the nth derivative of the phase spectrum $d^n\theta(\omega)/d\omega^n$ is determined by: calculating an nth derivative $d^n|H(\omega)|/d\omega^n$ of the acquired amplitude spectrum $|H(\omega)|$; and applying a phase-retrieval procedure on the $d^n|H(\omega)|/d\omega^n$, thereby determining the $d^n\theta(\omega)/d\omega^n$. Alternatively, the nth derivative of the phase spectrum $d^n\theta(\omega)/d\omega^n$ is determined by: calculating an nth derivative $d^n \ln(|H(\omega)|)/d\omega^n$ of the acquired amplitude spectrum $|H(\omega)|$; and applying a phase-retrieval procedure on the $d^n \ln(H(\omega))/d\omega^n$, thereby determining the $d^n\theta(\omega)/d\omega^n$. Any suitable phase-retrieval procedure may be applied, for example the Kramers-Kronig relation.

The $d^n\theta(\omega)/d\omega^n$ is then integrated n times to acquire an phase spectrum $\theta(\omega)$ of the complex spectral transfer function.

From $|H(\omega)|$ measured by detector 44 and the thus-determined phase spectrum $\theta(\omega)$, the complex spectral transfer function $H(\omega)$ of the volume of material is easily calculated since $\ln[H(\omega)] = \ln(|H(\omega)|) + i\theta(\omega)$.

The complex spectral transfer function $H(\omega)$ is a refractive index spectrum of the material with which the beam interacted.

Figure 9B:
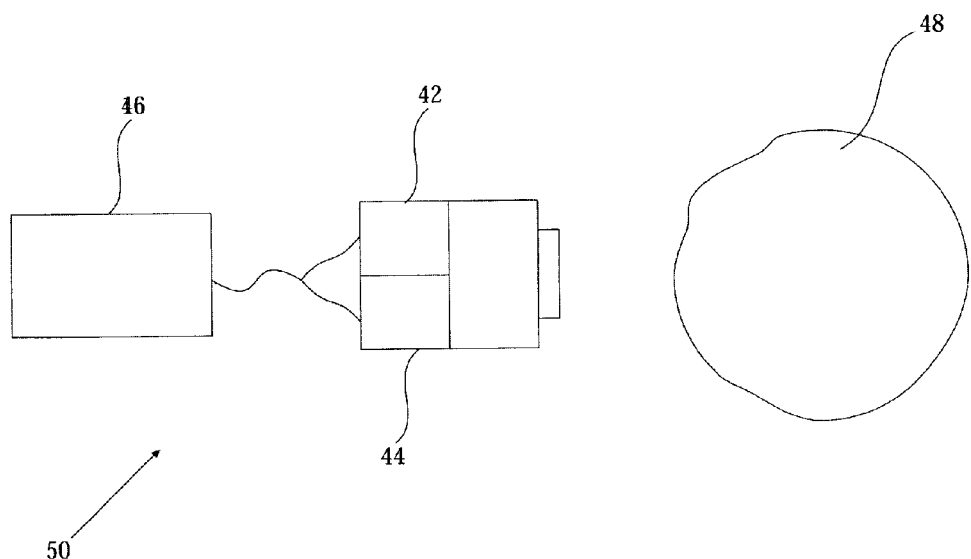

Device 40 depicted in FIG. 9A operates by detecting radiation projected through a volume of material making up object of interest 18. In some related embodiments, a device operates by detecting radiation reflected from a volume of material making up an object of interest. For example device 50 schematically depicted in FIG. 9B is used and substantially operates like device 40, except that the radiation detected by detector 44 is reflected from object of interest 48.

In some embodiments, object of interest 48 is transparent to some or all of the wavelengths of radiation in the beam projected by transmitter 42.

In some embodiments, object of interest 48 scatters some or all of the wavelengths of radiation in the beam projected by transmitter 42.

In some embodiments, the beam projected by a transmitter has only a single or few wavelengths of radiation at one time. In some embodiments, the beam projected by a transmitter comprises a plurality of wavelengths of radiation at one time.

Anchoring

Like in the embodiments above, in some embodiments the phase spectrum $\theta(\omega)$ of the complex spectral transfer function $H(\omega)$ approximated as described above is insufficient or it is desired that the approximation be even more accurate. In some such embodiments, the accuracy of the approximation of $\theta(\omega)$ is increased by at least partially directly measuring at least one value of the nth derivative of the phase spectrum $d^n\theta(\omega)/d\omega^n$; and using the measured values to improve the phase spectrum $\theta(\omega)$, substantially as described above using SPEBI.

Some specific implementations of embodiments of the invention are described hereinbelow.

Environmental Monitoring

In some embodiments, object of interest 48 is a portion of atmosphere or other gas, and a device 40 or 50 is used for monitoring, for example environmental monitoring. In some such embodiments, device 40 or 50 is intermittently or periodically activated to determine a refractive index spectrum of object of interest 48 to determine a change in composition of object of interest, for example the presence of pollutants. Since device 40 and especially 50 also operates in monitoring scattering media, such devices are exceptionally suitable for monitoring in all-weather conditions (including water-vapor, fog, mist, clouds, smoke, rain, haze, steam or dust) and for monitoring scattering media such as clouds or steam.

For example, in some embodiments, device 40 monitors the gas expelled from a smokestack of an industrial plant to determine that the released gases are not harmful. A change in a detected refractive index spectrum indicates that a pollutant has been accidentally released, allowing an operator to take a required action, for example activating a scrubber or shutting the plant down.

In some embodiments, a detected refractive index spectrum is compared to a library of stored refractive index spectra. For example, a library includes the refractive index spectrum of ammonia and steam. During operation, a detected refractive index spectrum is compared to the refractive index spectra stored in the library. As long as a detected spectrum substantially resembles the spectrum of steam, no particular action is taken. If the detected spectrum substantially resembles the spectrum of ammonia, a required action in the event of an apparent ammonia leak is taken.

Border Monitoring

A challenge known in the art is monitoring the passage of objects such as animals, people or vehicles into an area over a delineated border. One solution is projecting a beam of radiation from a transmitter to a detector in parallel to the border. An object crossing the border temporarily blocks the beam of radiation from detection by the detector, activating an alarm. Such solutions are ineffective when, for example due to inclement weather conditions, a scattering medium such as water-vapor, fog, mist, clouds, smoke, rain, haze, steam or dust screens the object while crossing the border.

In some embodiments, object of interest 48 is the volume between transmitter 42 and detector 44, and a device 40 or 50 is used for monitoring the passage of an object through a beam of radiation projected by transmitter 42. The device 40 or 50 is intermittently or periodically activated to determine a refractive index spectrum of the volume between transmitter 42 and detector 44. As long as the determined refractive index spectrum is "normal" that is to say corresponds to atmospheric conditions such as water-vapor, fog, mist, clouds, smoke, rain, haze, steam or dust, no particular action is taken. If the determined refractive index spectrum is abnormal, e.g., the beam of radiation projected by transmitter 42 is entirely blocked by an object, a required action is taken, for example a warning is sounded.

Material Characterization and Quality Control

In many fields, it is important to determine a refractive index spectrum of a material in order to characterize the material, for example, new materials or quality control of components in the field of optical components and semiconductors.

In some embodiments, object of interest 48 is a workpiece of material or a component during or subsequent to a manufacturing process, and a device 40 or 50 is used for determining a refractive index spectrum of object of interest 48. In some embodiments, the determining is for quality control, to ensure that object of interest 48 has at least the minimal material qualities. In some embodiments, the determining of for development, to evaluate of a new material, a new processing method or a new geometry provides required qualities.

Object of interest 48 is appropriately placed and device 40 or 50 is activated to determine a refractive index spectrum of object of interest 48. The determined refractive index spectrum is further used in the usual way in evaluating the value and/or utility of object of interest.

In a related embodiment, quality control of objects of interest that comprise scattering media (e.g., emulsions, suspensions and colloids) is a well-known challenge in industry. For example, milk is an emulsion that is susceptible to contamination for example with melamine, but is difficult to analyze due to the fact that milk if a scattering medium.

In some embodiments, a device such as 40 or 50 is integrated as a quality control component, for example in an industrial process. In some such embodiments, an object of interest 48 (e.g., individual workpieces such as bottles or bags filled with milk) are serially transported to a location relative to transmitter 42 and detector 44 where the device is able to determine a refractive index spectrum of the workpiece. If the determined refractive index spectrum is indicative of a faulty object of interest, appropriate action is taken.

Image Using Refractive Index Spectrum

In some embodiments, an image is assembled from the refractive index spectra of a plurality (at least two) of volumes defining an area of interest of an object, the volumes selected to correspond to the pixels of the image of the object.

In some such embodiments, an area of interest of an object is selected and a transmitter 42 and a detector 44 acquire an amplitude spectrum $|H(\omega)|$ of a complex spectral transfer function $H(\omega)$ of each one of a plurality of volumes, the plurality of volumes defining the area of interest of the object.

The volumes of the plurality of volumes are arranged in the usual way for assembling an image of the area of interest where each volume corresponds to a pixel in the image to be assembled.

$|H(\omega)|$ is acquired for each volume as described above. Subsequently, a refractive index spectrum of the material $H(\omega)$ of the material making up each volume is calculated, substantially as described above.

For display, a refractive index spectrum corresponding to each volume is displayed, as a pixel making up the image, so that the pixels taken together constitute an image of the area of interest. Analogous to the known in the art, each pixel is given an appearance so that pixels representing volumes having the same refractive index spectrum have the same appearance.

In some embodiments, the material in each volume is determined from a corresponding refractive index spectrum (for example, by comparison to a library of refractive index spectra) and the corresponding pixel given a distinctive appearance.

For example, in some embodiments where an object is the effluent from a smokestack, pixels corresponding to volumes consisting of water vapor appear having a first color (e.g., white) while pixels corresponding to volumes consisting of ammonia appear giving a second color (e.g., green).

For example, in some embodiments where an object is the torso of a human being, pixels corresponding to volumes consisting of a transparent material (e.g., the air surrounding the torso) appear having a first color, pixels corresponding to volumes consisting of a scattering material (e.g., fabric, biological tissue) appear having a second color and pixels corresponding to volumes consisting of materials that entirely block the passage of the radiation (e.g., metal objects) appear having a third color (e.g., black).

In some embodiments, transmitter 42 projects a beam of radiation at only one volume at any given time and detector 44 acquires $|H(\omega)|$ of only that volume. In some such embodiments, transmitter 42 and/or detector 44 are physically moved, e.g., using an X-Y table, to scan the plurality of volumes. In some such embodiments, the radiation projected by transmitter 42 is aimed, for example with an aiming assembly comprising lenses and mirrors to scan the plurality of volumes. In some such embodiments, the radiation projected by the transmitter subsequent to interaction with a volume is directed towards detector 44, for example with an aiming assembly comprising lenses and reflectors (e.g., mirrors) to scan the plurality of volumes.

In some embodiments, a transmitter 42 is configured to simultaneously project a beam of radiation at more than one volume, and even at an entire area of interest, for example, transmitter 42 the beam of radiation is wide beam. In some such embodiments, a corresponding detector 44 is configured to acquire the projected radiation subsequent to interaction with a volume from only one volume at a time. In some such embodiments, a corresponding detector 44 is configured to acquire the projected radiation subsequent to interaction with a volume from more than one volume at a time and even from an entire area of interest, for example a detector 44 comprises an array of individual detection elements, each detection element acquiring $|H(\omega)|$ of a volume subsequent to interaction with the volume of the medium.

Imaging in a Scattering Medium

As discussed in the introduction, a challenge is to detect, observe or image an object that is screened by a scattering medium.

Analogously to the disclosed in Refs. 10, 14-16, upon perusal of the description herein the teachings of the invention may be utilized for imaging of objects of interest screened by a scattering medium. In brief, the impulse response h(t) of each volume of the scattering medium is calculated from H($\omega$) found as described above. An image is assembled from the ballistic and, if needed, quasi-ballistic radiation as described in Refs. 10, 14-16 of the Inventors and as known in the art [Refs. 17-21]. Objects which are otherwise apparent with the used wavelengths of radiation but screened by the scattering of the radiation by the scattering medium, are apparent in the image and it therefore becomes possible to look into or through a scattering medium to detect, observe and image screened objects.

Importantly, the teachings of the invention allow detection, observation and imaging using radiation, especially electromagnetic radiation, especially electromagnetic radiation having optical frequencies that were heretofore unusable because of the presence of a scattering medium.

Thus, in some embodiments, an image is assembled from ballistic, and in some embodiments quasi-ballistic, radiation interacting with a plurality (at least two) of volumes defining an area of interest of a scattering medium, the volumes selected to correspond to the pixels of the image of the area of interest of the scattering medium.

In some such embodiments, as described for images assembled from refractive index spectra, an area of interest of the scattering medium is selected and a transmitter 42 and a detector 44 acquire an amplitude spectrum |H($\omega$)| of a complex spectral transfer function H($\omega$) of each one of a plurality of volumes, the plurality of volumes defining the area of interest of the object. H($\omega$) of each volume is calculated, substantially as described above, for example using DKK, DMSKK or MEM with SPEBI.

The calculated H($\omega$) is converted (for example, by inverse Fourier-transform) to h(t) the impulse-response of the volume. As described in the art [Refs. 17-21] the ballistic and, in some embodiments, quasi-ballistic radiation is recovered from h(t) for each volume of the area of interest that corresponds to a pixel, so that the pixels taken together constitute an image of the area of interest of the scattering medium. As described above, non-transparent objects screened by the scattering medium are apparent in the image.

In some embodiments, conversion of H($\omega$) to h(t) is performed by an appropriately configured signal analysis assembly, for example a signal analysis assembly such as 16 of a device of the invention such as 40 or 50.

In some embodiments, recovery of the ballistic, and if applicable, quasi-ballistic radiation, from h(t) is performed by an appropriately configured signal analysis assembly, for example a signal analysis assembly such as 46 of a device of the invention such as 40 or 50.

In some embodiments, display of the recovered radiation as an image is performed is performed by an appropriately configured signal analysis assembly, for example a signal analysis assembly such as 16 of a device of the invention such as 40 or 50, that comprises a display assembly, such as a display screen (e.g., CRT, LED, plasma screen).

The teachings of the invention may be implemented using radiation such as acoustic radiation and electromagnetic radiation of any wavelength, including gamma rays, X-ray, ultraviolet, visible, infrared and radio. That said, in some embodiments the teachings of the invention are preferably implemented using optical electromagnetic radiation, that is to say near UV (about 200 nm to about 400 nm), visible (about 380 nm to about 750 nm), near-infrared (from about 700 nm to about 2000 nm) and also midwave infrared (about 2000 nm to about 8000 nm), longwave infrared (about 8000 nm to about 15000 nm) and far infrared (about 15000 nm to about 300000 nm). As noted in the introduction, optical electromagnetic radiation is preferred as it includes large amounts of information, has excellent resolution, is generally safe and is useful because images acquired with optical electromagnetic radiation are "natural", include real color and are therefore relatively intuitive to understand.

Screening by Atmospheric Scattering Medium

A challenge in the art is the observation and imaging of objects screen by atmospheric scattering medium such as water-vapor, fog, mist, clouds, dust and smoke, for example, aircraft in or behind clouds or mist as well as people, vehicles and other objects in fog, mist, dust, haze or smoke. It is known to use radio waves as these are not scattered by atmospheric scattering media, but radio waves have extremely poor resolution making identification of an observed object and even discerning two nearby objects virtually impossible. In some embodiments of the invention, an image is acquired of atmospheric scattering medium allowing observation and imaging of objects screened by the atmospheric scattering medium. In some embodiments, the wavelengths of radiation projected by the transmitter comprise optical electromagnetic radiation, inter alia because in some embodiments such radiation provides excellent resolution.

Screening by Fibers

A common scattering medium comprises fibers, for example clothing. In the field of homeland security, there is a need to ensure that people do not carry weapons such as knives and firearms concealed by clothing. Known devices such as metal detectors do not provide an image of a metal object carried by a person, making it difficult to differentiate between a large belt buckle or steel-reinforced boots and a firearm. Other types of imaging such as X-ray based imaging may pose health risks. In some embodiments, an image is acquired of a scattering medium comprising fibers such as clothing allowing observation and imaging of objects screened by the fibers, for example in the field of homeland security. In some embodiments, the wavelengths of radiation projected by the transmitter comprise eye-safe optical electromagnetic radiation, inter alia because in some embodiments such radiation allows assembly of easily interpretable images.

Quality Control

Manufactured semiconductor components and optical elements may include defects that are screened due to the scattering of radiation by the material from which the semiconductor components and optical elements are made. In some embodiments, an image is acquired of a scattering medium comprising a semiconductor component or optical element, allowing observation and imaging of defects, for example in the field of industrial quality control. In some embodiments, the wavelengths of radiation projected by the transmitter comprise optical electromagnetic radiation especially near UV and also far UV and extreme UV light, inter alia because in some embodiments such radiation has a sufficiently short wavelength to allow sufficiently high resolution to observe typical defects.

Medical Imaging

Biological tissue such as skin, bone, fat muscle, blood and brain is a scattering medium. For that reason, it is not practical to directly look into the body and see abnormalities such as tumors.

It is known to use X-rays in medical imaging to differentiate between hard-tissue such as bones and soft tissue. X-rays are considered harmful and of limited utility for differentiating between different types of soft tissue such as tumors and health tissue.

An exceptional challenge is to acquire an image of soft tissue inside the skull, for example of brain tumors or other defects. Some embodiments of the invention relate to medical imaging, that is to say, the use of the teachings of the present invention to provide trans-tissue such as transcutaneous imaging, for example, to detect tumors and other pathologies.

In some embodiments of the invention, an image is acquired of biological tissue through a scattering medium that is biological tissue. In some embodiments, the wavelengths of radiation projected by the transmitter comprise optical electromagnetic radiation, inter alia because in some embodiments such radiation provides easily interpretable results. For example, in some embodiments, the teachings of the invention allow "seeing" through skin and fat layers to see tumors, for example, tumors of the breast. In some embodiments, tumors are readily apparent due to difference in the amount of blood to the tumors. In some embodiments, the teachings of the invention allow imaging through the skull, for example of brain tumors.

For some embodiments, for example some homeland security embodiments, a suitable transmitter projects electromagnetic radiation having eye-safe wavelengths between about 1530 and about 1560 nm, for example at 10 pm intervals for a total of 300 wavelengths for each volume.

For some embodiments, for example some medical imaging embodiments, a suitable transmitter projects electromagnetic radiation having wavelengths between about 700 and about 800 nm.

Optical Clearing

In some embodiments, it is advantageous to use optical clearing methods together with the teachings of the invention. Generally, optical clearing involves forcing a fluid optical clearing agent such as glycerol or aqueous glucose solutions into the skin and other biological tissue to reduce differences in refractive indices between tissue components, to reduce scattering and to increase transmittance of projected radiation passing therethrough. As a result, radiation projected into the skin for imaging in accordance with the teaching of the invention is able to penetrate deeper into the body. Optical clearing has been shown to improve the performance of imaging methods such as optical coherence tomography.

In some embodiments, the optical clearing agent is forced into the skin and other biological tissue with the help of ultrasonic energy.

Although embodiments of the invention have been described by way of illustration, it should be understood that the invention is a new non-interferometric method to improve the accuracy of a phase spectrum in many different applications and which may be carried out with many variations, modifications, and adaptations. In particular, the use of optical radiation in the discussions above are not meant to be a limitation, as the disclosed embodiments of the invention are suitable for any portion of the electromagnetic spectrum and also for implementation with non-electromagnetic radiation such as acoustic waves.

Implementation of the invention in improving the phase-spectrum that was derived from either the KK or MEM phase-retrieval algorithm has been described. However, in general, the disclosed differential phase-anchoring technique can be implemented to improve the accuracy of any phase spectrum that is based on partial information, where phase spectrums derived from phase-retrieval algorithms are just one example. For example, in some applications the phase can be directly measured for a finite number N of frequencies, where N is insufficient to give high accuracy in the desired frequency range. Then the disclosed differential phase-anchoring technique can be implemented to anchor the phase spectrum and thus to improve the accuracy within the desired frequency range. In addition, the descriptions herein of the embodiments using KK or MEM as phase-retrieval algorithms are meant to serve as particular examples. The approximate phase spectrum that is derived from any phase-retrieval method that is based upon any physical or mathematical assumption or criterion (e.g., the KK is based on causality and the MEM on maximum entropy) can be improved through the use of the disclosed differential phase-anchoring technique. The differential phase measurements are integrated into the reconstructed or partially measured phase spectrum (e.g. through a Lagrange polynomial as described for the MEM technique) to improve the reconstruction.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Citation or identification of any reference in this application shall not be construed as an admission that such reference is available as prior art to the invention.

Section headings are used herein to ease understanding of the specification and should not be construed as necessarily limiting.

BIBLIOGRAPHY

[1] R. Kronig, "On theory of dispersion of X-rays', J. Opt. Soc. Amer., 12, 547 (1926)

[2] H. A. Kramers, *Estratto dagli Atti del Congresso Internazionale di Fisici Como* (Nicolo Zonichello, Bologna, 1927).

[3] V. Lucarini, J. J. Saarinen, K.-E. Peiponen, and E. M. Vartiainen, "Kramers-Kronig Relations in Optical Materials Research", Springer-Verlag, Berlin 2005

[4] Granot and S. Sternklar, "Reconstructing the impulse response of a diffusive medium with the Kramers-Kronig relations", J. Opt. Soc. Am. B. 24, 1620-1626 (2007)

[5] L. Wang, P. P. Ho, F. Liu, G. Zhang, and R. R. Alfano, "Ballistic 2-D imaging through scattering walls using an ultrafast optical Kerr gate," Science 253, 769-771 (1991)

[6] J. C. Hebden and D. T. Delpy, "Enhanced time-resolved imaging with a diffusion model of photon transport," Opt. Lett. 19, 311 (1994)

[7] G. M. Turner, G. Zacharakis, A. Soubret, J. Ripoll, V. Ntziachristos, "Complete-angle projection diffuse optical tomography by use of early photons," Opt. Lett. 30, 409 (2005)

[8] A. Ya. Polishchuk, J. Dolne, F. Liu, and R. R. Alfano, "Average and most-probable photon paths in random media," Opt. Lett. 22, 430 (1997)

[9] L. Wang, X. Liang, P. Galland, P. P. Ho, and R. R. Alfano, "True scattering coefficients of turbid matter measured by early-time gating," Opt. Lett. 20, 913 (1995)

[10] E. Granot, S. Sternklar, D. Schermann, Y. Ben-Aderet, and M. H. Itzhaq, "200 femtosecond impulse response of a Fabry-Perot etalon with the spectral ballistic imaging technique", Appl. Phys. B 82, 359-362 (2006)

[11] R. Z. Bachrach and F. C. Brown, "Exciton-optical properties of TlBr and TlCl," Phys. Rev. B1, 818-831 (1970)

[12] R. K. Ahrenkiel, "Modified Kramers-Kronig analysis of optical spectra," J. Opt. Soc. Am. 61, 1651-1655 (1971)

[13] K. F. Palmer, M. Z. Williams, and B. A. Budde, "Multiply subtractive Kramers-Kronig analysis of optical data," Appl. Opt. 37, 2660-2673 (1998)

[14] E. Granot and S. Sternklar, "Spectral ballistic imaging: a novel technique for viewing through turbid or obstructing media", J. Opt. Soc. Am. A 20, 1595 (2003)

[15] E. Granot, S. Sternklar, Y. Ben-Aderet and D. Schermann, "Quasi-ballistic imaging through a dynamic scattering medium with optical-field averaging using Spectral-Ballistic-Imaging", Optics Express, 14, 8598-8603 (2006).

[16] E. Granot and S. Sternklar, PCT Patent Publication WO2004/008116.

[17] B. B. Das, F. Liu and R. R. Alfano, "Time-resolved fluorescence and photon migration studies in biomedical and model random media" Rep. Prog. Phys. 60, 227, (1997).

[18] J. C. Hebden "Evaluating the spatial resolution performance of a time-resolved optical imaging system" Med. Phys., 19, 1081 (1992).

[19] Q. Z. Wang, X. Liang, L. Wang, P. P. Ho and R. R. Alfano, "Fourier spatial filter acts as a temporal gate for light propagating through a turbid medium", Optics Letters, 20, 1498 (1995).

[20] E. N. Leith et al, "Realization of time gating by use of spatial filtering", Appl. Opt. 38, 1370 (1999).

[21] A. Kuditcher et al, "Ultrafast cross correlated harmonic imaging through scattering media", Appl. Opt. 40, 45 (2001).

[22] G. W. Milton, D. J. Eyre, and J. V. Mantese, "Finite Frequency Range Kramer Kronig Relations: Bounds on the Dispersion", Phys. Rev. Lett., 79, 3062 (1997).

[23] E. Granot, Y. Ben-Aderet, and S. Sternklar, "Differential multiply subtractive Kramers-Kronig relations," J. Opt. Soc. Am. B 25, 609-613 (2008).

The invention claimed is:

1. A method for determining a phase spectrum of a complex spectral transfer function of a medium, said method being implemented by a computer program, stored on a non-transitory computer readable medium and configured to execute on a computer, said method comprising the steps of:
   a. determining a derivative of said phase spectrum, to obtain a phase-derivative spectrum, from a measured amplitude of said complex spectral transfer function using a measuring instrument; and
   b. integrating, using said computer, said phase-derivative spectrum to acquire said phase spectrum, wherein the phase-derivative spectrum is determined from the amplitude of the spectral transfer function by:
      1. measuring the phase-derivative at one or more frequencies; and
      2. using said measured phase derivatives to reconstruct said phase-derivative spectrum for all frequencies in the spectral range,
   c. providing a radiation source adapted to produce an beam having a wide spectral width;
   d. using a modulator controlled by electrical signals from a signal generator to modulate said beam;
   e. causing said modulated beam to interact with said medium;
   f. using an arrangement adapted for collecting radiation to collect radiation that has interacted with said medium;
   g. using a beam divider to divide said collected radiation into two portions;
   h. using a device configured to measure the intensity of radiation having different spectral components to measure the amplitude spectrum of the first portion of said collected radiation;
   i. transferring said measured intensity spectrum to the computer;
   j. using a device configured to divide a beam of radiation into its spectral components to divide the second portion of said collected radiation;
   k. using one or more detectors to detect said spectral components of said second portion of collected radiation;
   l. using one or more phase detectors to measure the phase lags of the electrical signals from said one or more detectors relative to said electrical signals from said signal generator;
   m. transferring said measured phase lags to said computer; and
   n. supplying said measured amplitude spectrum and said measured phase lags as inputs to the computer program and to determine said phase spectrum of said medium from said inputs.

2. A method according to claim 1 wherein the phase spectrum is derived from a known amplitude spectrum by any known phase-retrieval procedure.

3. A method according to claim 1 wherein the phase spectrum is at least partially measured directly.

4. A method according to claim 1 wherein the medium is a diffusive medium that at least partially scatters the radiation in a diffuse manner.

5. A method according to claim 1, wherein, in step f, the radiation that is collected by said arrangement has been transmitted through the medium.

6. A method according to claim 1, wherein, in step f, the radiation that is collected by said arrangement has been reflected from the medium.

7. A method according to claim 1, wherein, in step n, the phase spectrum of the medium is determined by the steps of:
   1. substituting the measured amplitudes and the measured phase lags in a Differential Multiply-Subtractive Kramers-Kronig (DMSKK) formula to compute the phase differences; and
   2. performing a summation of said phase differences.

8. A method according to claim 1, wherein, in step n, the phase spectrum of the medium is determined by the steps of:
   1. substituting the measured amplitudes and the measured phase lags in a Maximum Entropy Model (MEM) formula to compute error-phase derivatives at anchoring points;
   2. computing a polynomial interpolating function from said error-phase derivatives;
   3. determining an error phase spectrum by integrating said polynomial interpolating function; and
   4. determining said full complex phase spectrum from said error phase spectrum.

9. A method according to claim 4 wherein said method allows for detection and imaging of objects embedded within the diffusive medium.

10. A method for determining a phase spectrum $\theta(w)$ of the complex spectral transfer function $H(\omega)$ of a volume of an object, where $\ln(|H(\omega)|) = \ln(|H(\omega)|) + i\,\theta(\omega)$, said method being implemented by a computer program, stored on a non-transitory computer readable medium and configured to execute on a computer, said method comprising:

a) acquiring an amplitude spectrum $|H(\omega)|$ of said complex spectral transfer function $H(\omega)$ of a of the volume of the object using a measuring instrument;

b) determining, using said computer, an nth derivative of the phase spectrum $d^n\theta(\omega)/d\omega^n$ of said complex spectral transfer function $H(\omega)$, from said acquired amplitude spectrum $|H(\omega)|$; and c) integrating, using said computer, said $d^n\theta(\omega)/d\omega^n$ n times to acquire an approximation of said phase spectrum $\theta(\omega)$ of the complex spectral transfer function, wherein n is an integer of at least 0.

11. The method of claim 10, wherein said nth derivative of the phase spectrum $d^n\theta(\omega)/d\omega^n$ is determined by:

calculating an nth derivative $d^n \ln(|H(\omega)|)/d\omega^n$ of said acquired amplitude spectrum $|H(\omega)|$; and applying a phase-retrieval procedure on said $d^n \ln|H(\omega)|/d\omega^n$, thereby determining said c.

* * * * *